(12) United States Patent
Park et al.

(10) Patent No.: US 9,017,336 B2
(45) Date of Patent: Apr. 28, 2015

(54) ARTHROPLASTY DEVICES AND RELATED METHODS

(75) Inventors: Ilwhan Park, Walnut Creek, CA (US); Stephen M. Howell, Elk Grove, CA (US); Charlie W. Chi, Milpitas, CA (US)

(73) Assignee: OtisMed Corporation, Alameda, CA (US)

( * ) Notice: Subject to any disclaimer, the term of this patent is extended or adjusted under 35 U.S.C. 154(b) by 1012 days.

(21) Appl. No.: 11/656,323

(22) Filed: Jan. 19, 2007

(65) Prior Publication Data

US 2007/0226986 A1     Oct. 4, 2007

Related U.S. Application Data

(60) Provisional application No. 60/780,757, filed on Mar. 9, 2006, provisional application No. 60/773,491, filed on Feb. 15, 2006.

(51) Int. Cl.
*A61B 17/58* (2006.01)
*A61B 17/15* (2006.01)
(Continued)

(52) U.S. Cl.
CPC ............... *A61B 17/154* (2013.01); *Y10T 29/49* (2015.01); *A61B 17/155* (2013.01); *A61B 17/157* (2013.01); *A61B 17/1675* (2013.01); *A61B 17/1764* (2013.01); *A61B 19/22* (2013.01); *A61B 2019/508* (2013.01); *A61B 17/1739* (2013.01); *A61B 17/1742* (2013.01); *A61B 2017/1778* (2013.01)

(58) Field of Classification Search
USPC ...................................... 606/79, 87; 600/587
See application file for complete search history.

(56) References Cited

U.S. PATENT DOCUMENTS 3,195,411 A   7/1965   MacDonald et al.
3,825,151 A   7/1974   Arnaud
(Continued)

FOREIGN PATENT DOCUMENTS

DE        3305237        2/1983
DE        4341367 C1     6/1995
(Continued)

OTHER PUBLICATIONS

Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
(Continued)

*Primary Examiner* — Christian Sevilla
(74) *Attorney, Agent, or Firm* — Polsinelli PC

(57) ABSTRACT

Arthroplasty jigs, arthroplasty jig blanks, and related methods and devices are disclosed. Some variations of the methods comprise forming an arthroplasty jig from a near-shape arthroplasty jig blank, where the near-shape arthroplasty jig blank has at least one feature specific to a target site to be matched by the arthroplasty jig. Certain of the methods comprise forming an arthroplasty jig having a first configuration from a near-shape arthroplasty jig blank having a second configuration approximating the first configuration. Some of the methods comprise forming a near-shape arthroplasty jig blank, where the near-shape arthroplasty jig blank is configured to be formed into an arthroplasty jig, and the near-shape arthroplasty jig blank has at least one feature specific to a target site to be matched by the arthroplasty jig.

37 Claims, 26 Drawing Sheets

(51) Int. Cl.
  *A61B 17/16* (2006.01)
  *A61B 17/17* (2006.01)
  *A61B 19/00* (2006.01)

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A | 5/1985 | Halcomb et al. |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A * | 3/1992 | Ferrante et al. ................. 606/88 |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |

(56) References Cited

U.S. PATENT DOCUMENTS

| | | |
|---|---|---|
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini et al. |
| D532,515 S | 11/2006 | Buttler et al. |
| 7,141,053 B2 | 11/2006 | Rosa et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,547,307 B2 | 6/2009 | Carson et al. |
| 7,548,638 B2 | 6/2009 | Graessner |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,643,862 B2 | 1/2010 | Schoenefeld |
| 7,660,623 B2 | 2/2010 | Hunter et al. |
| 7,693,321 B2 | 4/2010 | Lehtonen-Krause |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,787,932 B2 | 8/2010 | Vilsmeier et al. |
| 7,794,467 B2 | 9/2010 | McGinley et al. |
| D626,234 S | 10/2010 | Otto et al. |
| 7,806,896 B1 | 10/2010 | Bonutti |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| D642,263 S | 7/2011 | Park |
| 8,007,448 B2 | 8/2011 | Moctezuma De La Barrera |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,077,950 B2 | 12/2011 | Tsougarakis et al. |
| 8,086,336 B2 | 12/2011 | Christensen |
| 8,115,485 B1 | 2/2012 | Maier et al. |
| 8,126,234 B1 | 2/2012 | Edwards et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,165,657 B2 | 4/2012 | Krueger |
| 8,170,641 B2 | 5/2012 | Belcher |
| 8,170,716 B2 | 5/2012 | Coste-Maniere et al. |
| 8,177,850 B2 | 5/2012 | Rudan et al. |
| 8,202,324 B2 | 6/2012 | Meulink et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,949 B2 | 9/2012 | Haddad |
| 8,306,601 B2 | 11/2012 | Lang et al. |
| 8,311,306 B2 | 11/2012 | Pavlovskaia et al. |
| 8,323,288 B2 | 12/2012 | Zajac |
| 8,331,634 B2 | 12/2012 | Barth et al. |
| 8,337,501 B2 | 12/2012 | Fitz et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| D691,719 S | 10/2013 | Park |
| 8,545,509 B2 | 10/2013 | Park et al. |
| 8,617,171 B2 | 12/2013 | Park et al. |
| 8,617,175 B2 | 12/2013 | Park et al. |
| 8,734,455 B2 | 5/2014 | Park et al. |
| 8,737,700 B2 | 5/2014 | Park et al. |
| 8,801,719 B2 | 8/2014 | Park et al. |
| 8,828,011 B2 | 9/2014 | Park et al. |
| 8,882,779 B2 | 11/2014 | Park et al. |
| 2002/0055783 A1 | 5/2002 | Tallarida et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0176783 A1 | 9/2003 | Hu |
| 2003/0216669 A1 | 11/2003 | Lang et al. |
| 2004/0097952 A1 | 5/2004 | Sarin et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153066 A1 | 8/2004 | Coon et al. |
| 2004/0153079 A1 | 8/2004 | Tsougarakis et al. |
| 2004/0153087 A1 | 8/2004 | Sanford et al. |
| 2004/0171924 A1 | 9/2004 | Mire et al. |
| 2004/0204760 A1 | 10/2004 | Fitz et al. |
| 2004/0220583 A1 | 11/2004 | Pieczynski, II et al. |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0254584 A1 | 12/2004 | Sarin et al. |
| 2005/0021039 A1* | 1/2005 | Cusick et al. .................. 606/88 |
| 2005/0054914 A1 | 3/2005 | Duerk et al. |
| 2005/0059978 A1 | 3/2005 | Sherry et al. |
| 2005/0065617 A1 | 3/2005 | Moctezuma de la Barrera |
| 2005/0080426 A1 | 4/2005 | Qian |
| 2005/0096535 A1 | 5/2005 | Moctezuma de la Barrera |
| 2005/0113841 A1 | 5/2005 | Sheldon et al. |
| 2005/0119664 A1 | 6/2005 | Carignan et al. |
| 2005/0148843 A1* | 7/2005 | Roose .................. 600/407 |
| 2005/0148860 A1 | 7/2005 | Liew et al. |
| 2005/0149091 A1 | 7/2005 | Tanamal et al. |
| 2005/0192588 A1 | 9/2005 | Garcia |
| 2005/0216024 A1 | 9/2005 | Massoud |

(56) References Cited

U.S. PATENT DOCUMENTS

| | | |
|---|---|---|
| 2005/0234461 A1* | 10/2005 | Burdulis et al. .................. 606/79 |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015109 A1 | 1/2006 | Haines |
| 2006/0015188 A1 | 1/2006 | Grimes |
| 2006/0030853 A1 | 2/2006 | Haines |
| 2006/0036257 A1 | 2/2006 | Steffensmeier |
| 2006/0079755 A1 | 4/2006 | Stazzone et al. |
| 2006/0110017 A1 | 5/2006 | Tsai et al. |
| 2006/0111628 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0195113 A1 | 8/2006 | Masini |
| 2006/0244448 A1 | 11/2006 | Ballon et al. |
| 2006/0271058 A1 | 11/2006 | Ashton et al. |
| 2006/0293681 A1 | 12/2006 | Claypool et al. |
| 2007/0005073 A1 | 1/2007 | Claypool et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0106389 A1 | 5/2007 | Croxton et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173853 A1 | 7/2007 | MacMillan |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0213738 A1 | 9/2007 | Martin et al. |
| 2007/0219560 A1 | 9/2007 | Hodorek |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0237372 A1 | 10/2007 | Chen et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0125114 A1 | 5/2009 | May et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0209884 A1 | 8/2009 | Van Vorhis et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0234217 A1 | 9/2009 | Mire et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0145344 A1 | 6/2010 | Jordan et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0191242 A1 | 7/2010 | Massoud |
| 2010/0198351 A1 | 8/2010 | Meulink |
| 2010/0209868 A1 | 8/2010 | De Clerck |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2011/0015636 A1 | 1/2011 | Katrana et al. |
| 2011/0016690 A1 | 1/2011 | Narainasamy et al. |
| 2011/0029093 A1 | 2/2011 | Bojarski et al. |

(56) References Cited

U.S. PATENT DOCUMENTS

| | | |
|---|---|---|
| 2011/0029116 A1 | 2/2011 | Jordan et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0345845 A1 | 12/2013 | Park et al. |
| 2014/0005997 A1 | 1/2014 | Park |
| 2014/0378978 A1 | 12/2014 | Park |

FOREIGN PATENT DOCUMENTS

| | | |
|---|---|---|
| DE | 10 2005 023 028 A1 | 11/2006 |
| EP | 0097001 A1 | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |
| EP | 1486900 | 12/2004 |
| EP | 1 532 939 A1 | 5/2005 |
| EP | 1669033 A1 | 6/2006 |
| GB | 2215610 | 9/1989 |
| GB | 2420717 A | 6/2006 |
| GB | 2447702 A | 9/2008 |
| JP | 10-94538 | 4/1998 |
| JP | 2001-092950 | 4/2001 |
| WO | WO-93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 98/32384 | 7/1998 |
| WO | WO 00/35346 | 6/2000 |
| WO | WO-01/00096 A1 | 1/2001 |
| WO | WO-01/70142 A1 | 9/2001 |
| WO | WO 01/85040 A1 | 11/2001 |
| WO | WO 02/096268 A2 | 12/2002 |
| WO | WO-2004/032806 A1 | 4/2004 |
| WO | WO-2004/049981 A2 | 6/2004 |
| WO | WO-2004/049981 A3 | 6/2004 |
| WO | WO-2005/051240 A1 | 6/2005 |
| WO | WO 2005/087125 A2 | 9/2005 |
| WO | WO-2006/058057 A2 | 6/2006 |
| WO | WO-2006/060795 A1 | 6/2006 |
| WO | WO-2006/092600 A1 | 9/2006 |
| WO | WO 2006/127486 A2 | 11/2006 |
| WO | WO 2006/134345 A1 | 12/2006 |
| WO | WO-2007/014164 A2 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2008/091358 A1 | 7/2008 |

OTHER PUBLICATIONS

Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.

Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.

Barequet et al., "Filling Gaps in the Boundary of a Polyhedron," *Computer Aided Geometric Design*, vol. 12, pp. 207-229, 1995.

Barequet et al., "Repairing CAD Models," Proceedings of the 8th IEEE Visualization '97 Conference, pp. 363-370, Oct. 1997.

Biščević et al., "Variations of Femoral Condyle Shape," *Coll. Antropol.*, vol. 29 No. 2, pp. 409-414, 2005.

Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.

Couglin et al., "Tibial Axis and Patellar Position Relative to the Femoral Epicondylar Axis During Squatting," *The Journal of Arthroplasty*, vol. 18, No. 8, Elsevier, 2003.

Eckhoff et al., "Three-Dimensional Mechanics, Kinematics, and Morphology of the Knee Viewed in Virtual Reality," *The Journal of Bone and Joint Surgery*, vol. 87-A, Supplement 2, pp. 71-80, 2005.

(56) References Cited

OTHER PUBLICATIONS

Erikson, "Error Correction of a Large Architectural Model: The Henderson County Courthouse," Technical Report TR95-013, Dept. of Computer Science, University of North Carolina at Chapel Hill, pp. 1-11, 1995.

Ervin et al., *Landscape Modeling*, McGraw-Hill, New York, NY, 8 pages (Table of Contents), 2001.

Farin, *NURB Curves and Surfaces: From Projective Geometry to Practical Use*, AK Peters, Wellesley, MA, 7 pages (Table of Contents), 1995.

Fleischer et al., "Accurate Polygon Scan Conversion Using Half-Open Intervals," *Graphics Gems III*, pp. 362-365, code: pp. 599-605, 1992.

Grüne et al., "On numerical algorithm and interactive visualization for optimal control problems," *Journal of Computation and Visualization in Science*, vol. 1, No. 4, pp. 221-229, Jul. 1999.

Guéziec et al., "Converting Sets of Polygons to Manifold Surfaces by Cutting and Stitching," Proc. IEEE Visualization 1998, pp. 383-390, Oct. 1998.

Jones et al., "A new approach to the construction of surfaces from contour data," *Computer Graphics Forum*, vol. 13, No. 3, pp. 75-84, 1994 [ISSN 0167-7055].

Khorramabadi, "A Walk Through the Planned CS Building," Technical Report UCB/CSD 91/652, Computer Science Department, University of California at Berkeley, 74 pages, 1991.

Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Lorensen et al., "Marching Cubes: A High Resolution 3d Surface Construction Algorithm," *Computer Graphics*, vol. 21, No. 4, pp. 163-169, 1987.

Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.

Rohlfing et al., "*Quo Vadis*, Atlas-Based Segmentation?", *The Handbook of Medical Image Analysis: Segmentation and Registration Models* (Kluwer), pp. 1-55, (http://www.stanford.edu/~rohlfing/publications/2005-rohlfing-chapter-quo_vadis_atlas_based_segmentation.pdf).

Office Action, U.S. Appl. No. 10/146,862, mailed Jan. 13, 2005, 10 pages.

Amendment and Response to Office Action and Petition to Revive, U.S. Appl. No. 10/146,862, filed Jan. 18, 2006, 29 pages.

International Search Report and Written Opinion, PCT/US2007/001624, dated Dec. 12, 2007, 14 pages.

International Search Report and Written Opinion, PCT/US2007/001622, dated Jun. 11, 2007, 14 pages.

Restriction Requirement, U.S. Appl. No. 11/641,569, mailed Apr. 27, 2009, 7 pages.

International Search Report and Written Opinion, International Application No. PCT/US2009/34983, mailed May 22, 2009, 15 pages.

International Search Report and Written Opinion, International Application No. PCT/US2009/034967, mailed Jun. 16, 2009, 15 pages.

International Search Report and Written Opinion, International Application No. PCT/US2009/041519, mailed Jun. 17, 2009, 10 pages.

Kunz et al., "Computer Assisted Hip Resurfacing Using Individualized Drill Templates," The Journal of Arthroplasty, vol. 00, No. 0, pp. 1-7, 2009.

Akenine-Moller, T. et al. (2002). *Real-Time Rendering, Second Edition*. AK Peters: Natick, MA. six pages (Table of Contents).

Berry, E. et al. (2005). "Personalized Image-Based Templates for Intra-Operative Guidance," *Proc. Inst. Mech. Eng Part H: J. Engineering in Medicine* 219:111-118.

Blinn, J. (1996). *Jim Blinn's Corner—A Trip Down the Graphics Pipeline*. Morgan Kaufmann Publishers, Inc.: San Francisco, CA, five pages (Table of Contents).

Chauhan, S.K. et al. (Apr. 2004). "Computer-Assisted Knee Arthroplasty Versus a Conventional Jig-Based Technique, A Randomised, Prospective Trial," *The Journal of Bone and Joint Surgery* 86-B(3):372-377.

Cohen, M.F. et al. (1993). *Radiosity and Realistic Image Synthesis*. Academic Press Professional: Cambridge, MA, eight pages (Table of Contents).

Delp, S.L. et al. (Sep. 1998). "Computer Assisted Knee Replacement," *Clinical Orthopaedics and Related Research* 354:49-56.

Dutre, P. et al. (2003). *Advanced Global Illumination*. AK Peters: Natick, MA, five pages (Table of Contents).

Foley, J.D. et al. (1990). *Computer Graphics Principles and Practice, Second Edition*. Addison-Wesley Publishing Company: Reading, MA, nine pages. (Table of Contents).

Glassner, A.S. ed. (1989). *An Introduction to Ray Tracing*. Academic Press Inc.: San Diego, CA, four pages (Table of Contents).

Glassner. A.S. (1995). *Principles of Digital Image Synthesis*. Morgan Kaufmann Publishers, Inc.: San Francisco, CA, thirty-two pages (Table of Contents).

Gooch, B. et al. (2001). *Non-Photorealistic Rendering*. AK Peters: Natick, MA, four pages. (Table of Contents).

Hafez, M.A. et al. (Oct. 20-22, 2005). "Patient Specific Instrumentation for TKA: Testing the Reliability Using a Navigational System," *MIS Meets CAOS Symposium & Instructional Academy, Less and Minimally Invasive Surgery for Joint Arthroplasty: Fact and Fiction Syllabus*: San Diego, CA, 8 pages.

Hafez, M.A. et al. (2004). "Computer Assisted Total Knee Replacement: Could a Two-Piece Custom Template Replace the Complex Conventional Instrumentations?" *Computer Aided Surgery* 9(3):93-94.

Hafez, M.A. et al. (2006). "Computer-Assisted Total Knee Arthroplasty Using Patient-Specific Templating," *Clinical Orthopaedics and Related Research* 0:1-9.

Jensen, H.W. (2001). *Realistic Image Synthesis Using Photon Mapping*. AK Peters: Natick, MA, seven pages (Table of Contents).

Kidder, J. et al. (Nov. 21-22, 1996). "3-D Model Acquisition, Design, Planning and Manufacturing of Orthopaedic Devices: A Framework," In *Advanced Sensor and Control-System Interface*. B.O. Nnaji ed., Proceedings SPIE—The International Society for Optical Engineering: Bellingham, WA, pp. 9-22.

Pharr, M. et al. (2004). *Physically Based Rendering, From Theory to Implementation*. Morgan Kaufmann Publishers: San Francisco, CA, thirteen pages (Table of Contents).

Platt, G. et al. (Feb. 1969). "Mould Arthroplasty of the Knee, A Ten-Year Follow-Up Study," *The Journal of Bone and Joint Surgery British* vol. 51-B(1):76-87.

Potter, T.A. (Aug. 1969). "Arthroplasty of the Knee With Tibial Metallic Implants of the McKeever and MacIntosh Design," *The Surgical Clinics of North America* 49(4):903-915.

Radermacher, K. et al. (Sep. 1998). "Computer Assisted Orthopaedic Surgery With Image-Based Individual Templates," *Clinical Orthopaedics and Related Research* 354:28-38.

Shirley, P. et al. (2003). *Realistic Ray Tracing, Second Edition*. AK Peters: Natick, MA, seven pages (Table of Contents).

Strothotte, T. et al. (2002). *Non-Photorealistic Computer Graphics, Modeling, Rendering, and Animation*. Morgan Kaufmann Publishers: San Francisco, CA, nine pages (Table of Contents).

U.S. Appl. No. 10/146,862, filed May 15, 2002, for Park et al.

U.S. Appl. No. 11/642,385, filed Dec. 19, 2006, for Park et al.

Vande Berg, B.C. et al. (Feb. 2002). "Assessment of Knee Cartilage in Cadavers with Dual-Detector Spiral CT Arthrography and MR Imaging," *Radiology* 222(2):430-436.

Wikipedia, the Free Encyclopedia. (Date Unknown). "CNC," located at <http://en.wikipedia.org/wiki/CNC>, last visited on Apr. 12, 2007, 6 pages.

International Search Report and Written Opinion, International Application No. PCT/US2009/040629, mailed Aug. 6, 2009, 9 pages.

Restriction Requirement, U.S. Appl. No. 11/641,382, mailed Sep. 3, 2009, 6 pages.

(56) References Cited

OTHER PUBLICATIONS

Restriction Requirement, U.S. Appl. No. 11/642,385, mailed Oct. 27, 2009, 7 pages.
International Search Report and Written Opinion, International Application No. PCT/US2009/051109, mailed Nov. 6, 2009, 13 pages.
NonFinal Office Action, U.S. Appl. No. 11/641,569, mailed Nov. 12, 2009, 9 pages.
Invitation to Pay Additional Fees mailed on Jul. 31, 2007, for PCT Application No. PCT/US2007/001624 filed on Jan. 19, 2007, five pages.
International Search Report and Written Opinion, International Patent Application No. PCT/US2008/083125, dated Mar. 9, 2009, 13 pages.
U.S. Appl. No. 13/488,505, filed Jun. 5, 2012, Ilwhan Park et al.
Advisory Action and Interview Summary, U.S. Appl. No. 12/390,667, mailed Apr. 27, 2012, 23 pages.
Appeal Brief, U.S. Appl. No. 12/390,667, filed Jul. 12, 2012, 32 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 11/641,382, mailed Jul. 25, 2012, 12 pages.
Final Office Action, U.S. Appl. No. 11/641,569, mailed Mar. 1, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Non-Final Office Action, U.S. Appl. No. 11/641,569, dated Aug. 3, 2011, 14 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 11/641,382, mailed Mar. 29, 2012, 24 pages.
Non-Final Office Action, U.S. Appl. No. 11/946,002, dated Nov. 25, 2011, 44 pages.
Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/391,008, mailed Oct. 31, 2011, 44 pages.
Non-Final Office Action, U.S. Appl. No. 12/546,545, mailed Jul. 19, 2012, 28 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 13/066,568, mailed Oct. 26, 2011, 28 pages.
Notice of Allowance, U.S. Appl. No. 11/959,344, mailed Mar. 5, 2012, 13 pages.
Notice of Allowance, U.S. Appl. No. 12/386,105, mailed Jul. 5, 2012, 11 pages.
Office Action (Restriction Requirement), U.S. Appl. No. 12/563,809, dated Feb. 2, 2012, 7 pages.
Response to Final Office Action, U.S. Appl. No. 11/641,569, filed Jun. 28, 2012, 10 pages.
Response to Final Office Action, U.S. Appl. No. 11/959,344, filed Dec. 27, 2011, 16 pages.
Response to Final Office Action, U.S. Appl. No. 12/390,667, filed Mar. 12, 2012, 19 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/111,924, mailed Mar. 19, 2012, 8 pages.
Restriction Requirement, U.S. Appl. No. 12/386,105, dated Oct. 24, 2011, 7 pages.
Restriction Requirement, U.S. Appl. No. 12/391,008, dated Aug. 18, 2011, 6 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
U.S. Appl. No. 13/573,662, filed Oct. 2, 2012, Pavlovskaia et al.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Amendment Under 37 C.F.R. 1.312, U.S. Appl. No. 12/386,105, filed Oct. 1, 2012, 6 pages.
Appeal Brief, U.S. Appl. No. 12/391,008, filed Oct. 16, 2012, 24 pages.
Non-Final Office Action, U.S. Appl. No. 12/390,667, mailed Sep. 26, 2012, 21 pages.
Non-Final Office Action, U.S. Appl. No. 12/563,809, mailed Sep. 21, 2012, 32 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 13/374,960, mailed Nov. 2, 2012, 24 pages.
RCE/Amendment, U.S. Appl. No. 11/946,002, filed Sep. 6, 2012, 38 pages.

(56) References Cited

OTHER PUBLICATIONS

Response to Final Office Action, U.S. Appl. No. 11/641,382, filed Sep. 24, 2012, 11 pages.
Response to Final Office Action, U.S. Appl. No. 11/924,425, filed Sep. 5, 2012, 9 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Advisory Action, U.S. Appl. No. 11/642,385, dated Oct. 29, 2010, 3 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response, U.S. Appl. No. 11/642,385, filed May 28, 2010, 11 pages.
Final Office Action and PTO-892, U.S. Appl. No. 11/641,382, mailed Aug. 5, 2010, 13 pages.
Final Office Action, U.S. Appl. No. 11/641,569, mailed May 10, 2010, 9 pages.
International Preliminary Report on Patentability, PCT/US2009/034983, dated Sep. 10, 2010, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
Non-Final Office Action and PTO-892, U.S. Appl. No. 11/641,382, mailed Jan. 20, 2010, 12 pages.
NonFinal Office Action and PTO-892, U.S. Appl. No. 11/642,385, mailed Mar. 2, 2010, 11 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010.
RCE/Amendment, U.S. Appl. No. 11/642,382, filed Oct. 26, 2010, 14 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Restriction Requirement, U.S. Appl. No. 29/296,687, mailed Sep. 21, 2010, 7 pages.
Restriction Requirement, U.S. Appl. No. 11/959,344, dated Oct. 29, 2010, 6 pages.
Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume In Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clinical Orthopaedics and Related Research 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical Orthopaedics and Related Research 2003(410):35-43.
Freeman et al., "The Movement of the Normal Tibio-Femoral Joint," Journal Biomech. 2005;38(2):197-208.
Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "Least Squares 3D Surface and Curve Matching," ISPRS Journal of Photogrammetry & Remote Sensing, 59(2005), 151-174.
Hollister et al., "The Axes of Rotation of the Knee," Clinical Orthopaedics and Related Research 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.

(56) References Cited

OTHER PUBLICATIONS

Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Model Determination of the Tibia Based on 2d Radiographs Using a 2d/3d Database", Dept. of Surgery, Trauma Unit, University Hospital, Basel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):2733.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer-and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
Examiner's Answer in appeal, U.S. Appl. No. 12/391,008, mailed Dec. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Non-Final Office Action, U.S. Appl. No. 11/641,569, dated Jan. 3, 2013, 12 pages.
Non-Final Office Action, U.S. Appl. No. 13/086,275, mailed Feb. 7, 2013, 36 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.
Response to Non-Final Office Action, U.S. Appl. No. 12/563,809, filed Dec. 13, 2012, 15 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
Amendment and Response to Ex Parte Quayle Action, U.S. Appl. No. 29/296,687 dated Mar. 24, 2011, 17 pages.
Amendment and Response to Non-Final Office Action, U.S. Appl. No, 11/959,344, dated Jul. 15, 2011, 13 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
International Search Report and Written Opinion, PCT/US2011/032342, dated Jul. 1, 2011, 8 pages.
Nonfinal Office Action, U.S. Appl. No. 11/959,344, dated Feb. 15, 2011, 29 pages.
Notice of Allowance, U.S. Appl. No. 29/296,687, mailed Mar. 31, 2011, 18 pages.
RCE/Amendment, U.S. Appl. No. 11/642,385, filed Dec. 6, 2010, 13 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Restriction Requirement, U.S. Appl. No. 12/390,667, dated Jul. 14, 2011, 9 pages.
Amendment Under 37 C.F.R. 1.312, U.S. Appl. No. 13/374,960, filed May 7, 2013, 6 pages.
Audette et al. "An algorithmic overview of surface registration techniques for medical imaging." Medical Image Analysis, vol. 4, No. 3, Sep. 1, 2000, pp. 201-217.
European Search Report, EP09739422.5, dated Mar. 28, 2013, 9 pages.

(56) References Cited

OTHER PUBLICATIONS

Final Office Action, U.S. Appl. No. 11/641,569, dated Nov. 29, 2013, 20 pages.
Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 12/563,809, mailed Mar. 7, 2013, 14 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Ibáñez et al., The ITK Software Guide, Second Edition, Updated for ITK version 2.4, Nov. 21, 2005, pp. 114, 396-411, and 426.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/946,002, dated Oct. 2, 2013, 39 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/546,545, mailed Mar. 13, 2013, 10 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/723,904, mailed Aug. 9, 2013, 6 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, mailed May 24, 2013, 16 pages.
Notice of Allowance, U.S. Appl. No. 12/111,924, mailed Mar. 11, 2013, 14 pages.
Notice of Allowance, U.S. Appl. No. 12/546,545, dated Dec. 26, 2013, 9 pages.
Notice of Allowance, U.S. Appl. No. 12/563,809, mailed May 28, 2013, 11 pages.
Notice of Allowance, U.S. Appl. No. 12/636,939, dated Oct. 7, 2013, 28 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Preliminary Amendment, U.S. Appl. No. 13/731,697, filed May 10, 2013, 6 pages.
Response to Final Office Action, U.S. Appl. No. 12/546,545, filed Feb. 20, 2013, 13 pages.
Response to Final Office Action, U.S. Appl. No. 12/390,667, dated Dec. 23, 2013, 5 pages.
Response to Final Office Action, U.S. Appl. No. 12/563,809, filed May 6, 2013, 15 pages.
Response to Final Office Action, U.S. Appl. No. 12/546,545, dated Dec. 9, 2013, 8 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Restriction Requirement, U.S. Appl. No. 12/760,388, filed Apr. 5, 2013, 7 pages.
Restriction Requirement, U.S. Appl. No. 12/760,388, mailed Mar. 6, 2013, 7 pages.
Xie et al. "Segmentation by surface-to-image registration." proceedings of SPIE, vol. 6144, Mar. 2 2006, pp. 614405-1-614405-7.
U.S. Appl. No. 13/960,498, filed Aug. 6, 2013, Song.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
U.S. Appl. No. 14/272,147, filed May 7, 2014, Park et al.
U.S. Appl. No. 14/335,431, filed Jul. 18, 2014, Park et al.
U.S. Appl. No. 14/335,460, filed Jul. 18, 2014, Park et al.
Advisory Action, U.S. Appl. No. 11/642,385, dated Aug. 1, 2014.
Canadian Office Action, Appl. No. 2708393, dated Jul. 29, 2014.
European Search Report, EP 09835583.7, dated May 9, 2014.
European search Report, European Appl. No. 08863202.1, dated May 16, 2014.
Extended European Search Report, European Appl. No. 13188389.4, dated Jan. 8, 2014.
Final Office Action, U.S. Appl. No. 11/642,385, dated Apr. 25, 2014.
Japanese Office Action, JP Application No. 2011-507530, dated Dec. 17, 2013, 8 pages.
Non-Final Office Action, U.S. Appl. No. 11/946,002, dated Feb. 6, 2014, 46 pages.
Non-Final Office Action, U.S. Appl. No. 13/488,505, dated Jul. 17, 2014.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/760,388, dated Jan. 22, 2014, 13 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Preliminary Amendment, U.S. Appl. No. 13/731,850, filed Apr. 11, 2014, 8 pages.
Response to Final Office Action, U.S. Appl. No. 11/641,569, dated Jan. 29, 2014, 10 pages.

(56) References Cited

OTHER PUBLICATIONS

Response to Final Office Action, U.S. Appl. No. 11/642,385, dated Jul. 22, 2014.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Restriction, U.S. Appl. No. 13/488,505, dated May 5, 2014, 7 pages.
Restriction Requirement, U.S. Appl. No. 13/488,505, dated Mar. 4, 2014, 5 pages.
Siemens MAGNETOM Sonata 1.5T Technical Specifications, pp. 1-4, accessed online Jan. 28, 2014.
Supplementary European Search Report and Opinion, EP 09739474.6, dated Feb. 27, 2014, 7 pages.
Appeal Brief, U.S. Appl. No. 11/642,385, dated Oct. 7, 2014.
European Search Report, EP09823986.6, dated Sep. 23, 2014.
Final Office Action, U.S. Appl. No. 11/946,002, dated Sep. 17, 2014.
International Search Report and Written Opinion, PCT/US2014/030496, dated Aug. 6, 2014.
Response to Restriction, U.S. Appl. No. 13/749,095, dated Nov. 13, 2014.
Restriction Requirement, U.S. Appl. No. 13/749,095, dated Sep. 25, 2014.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al.. "Prediction of Total Knee Motion Using a Three-Dimensional Computer-Graphics Model." *J. Biomechanics*, vol. 23, No. 1, pp. 45-58, 1990.
Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Walker, P. S. et al. "Range of Motion in Total Knee Arthroplasty: A Computer Analysis." *Clinical Orthopaedics and Related Research*, No. 262, Jan. 1991.
Non-Final Office Action, U.S. Appl. No. 13/731,697, dated Jan. 29, 2015.
Non-Final Office Action, U.S. Appl. No. 13/749,095, dated Jan. 27, 2015.
Reply Brief, U.S. Appl. No. 11/642,385, dated Jan. 23, 2015.
Restriction Requirement, U.S. Appl. No. 14/476,500, dated Feb. 25, 2015.

\* cited by examiner

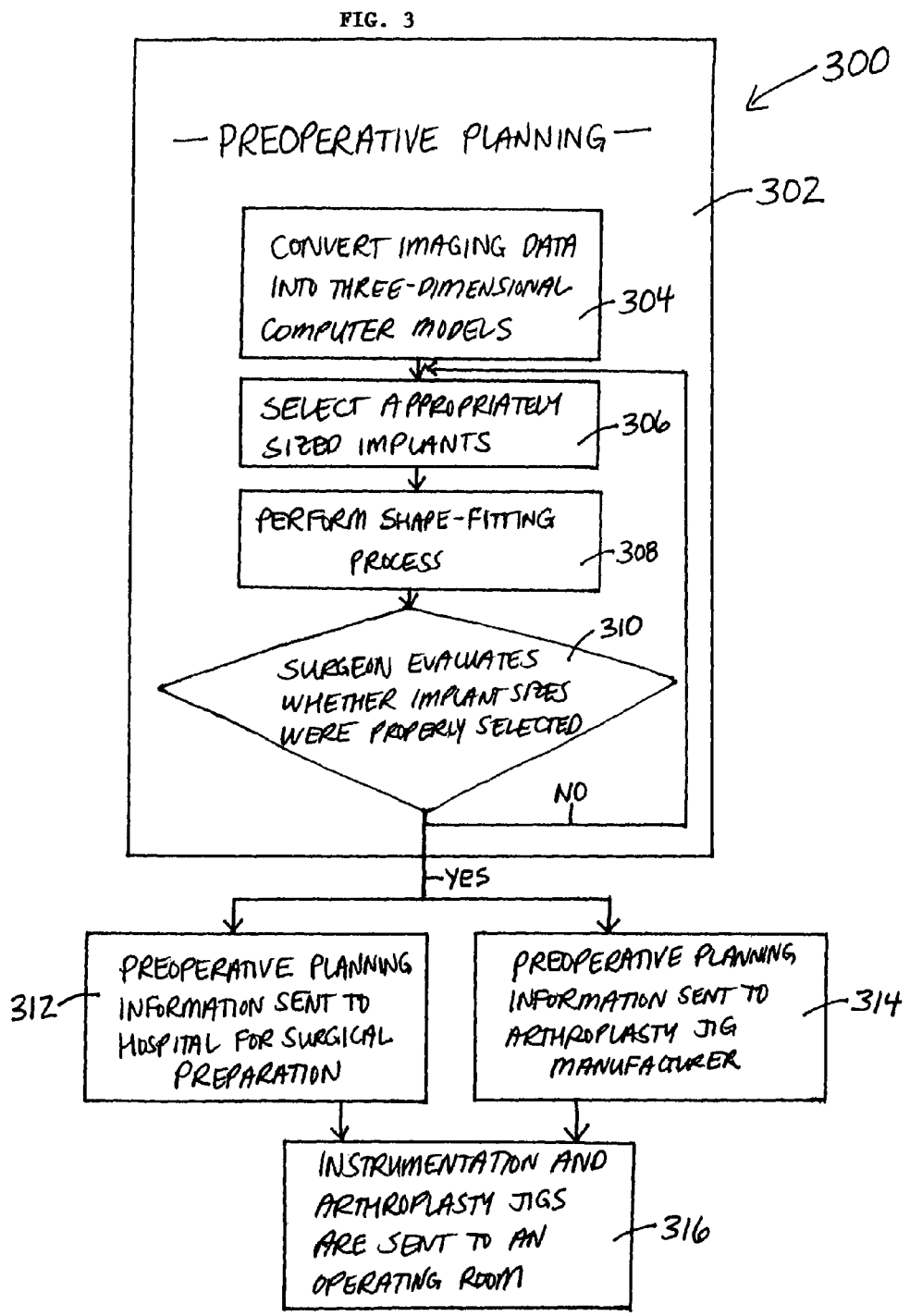

FIG. 6A
FIG. 6B
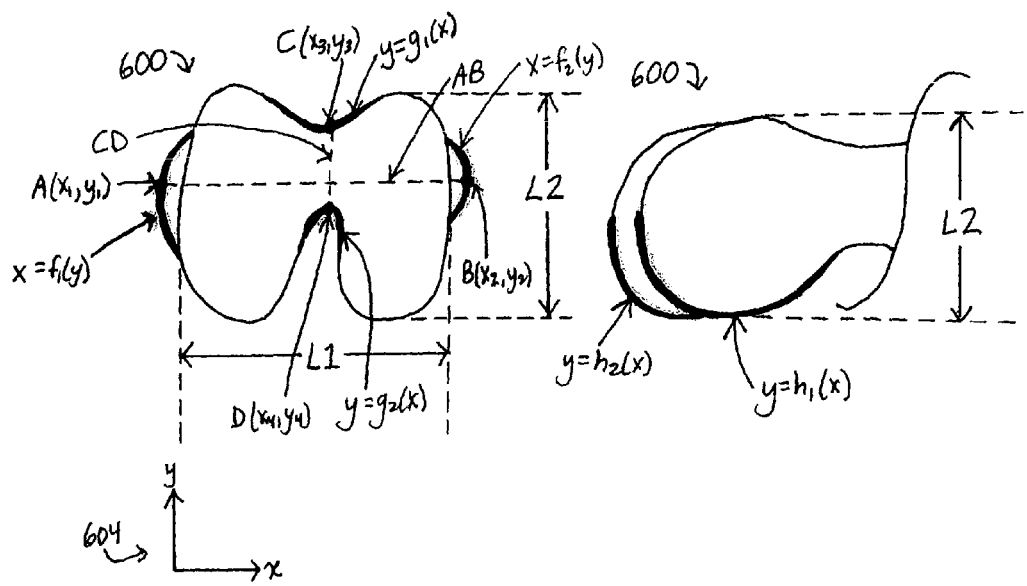
FIG. 6C
FIG. 6D
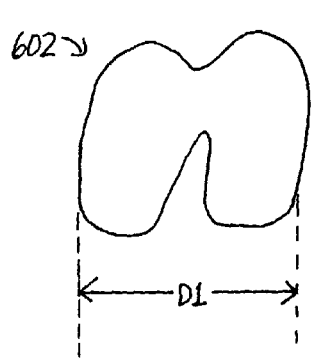
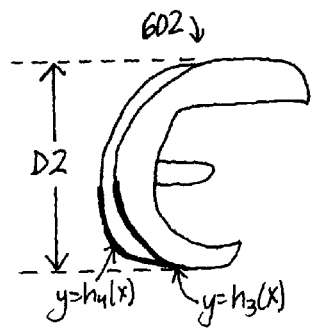

FIG. 6E
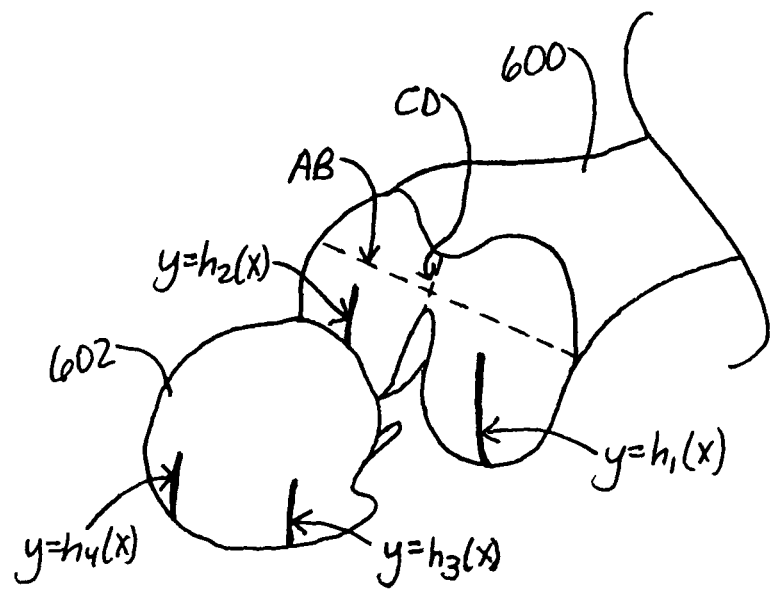
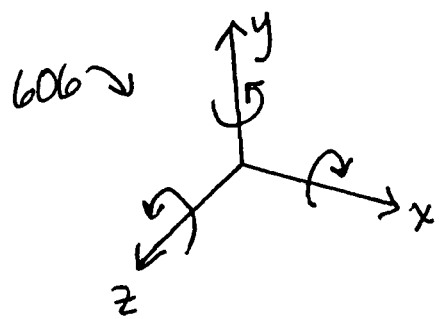

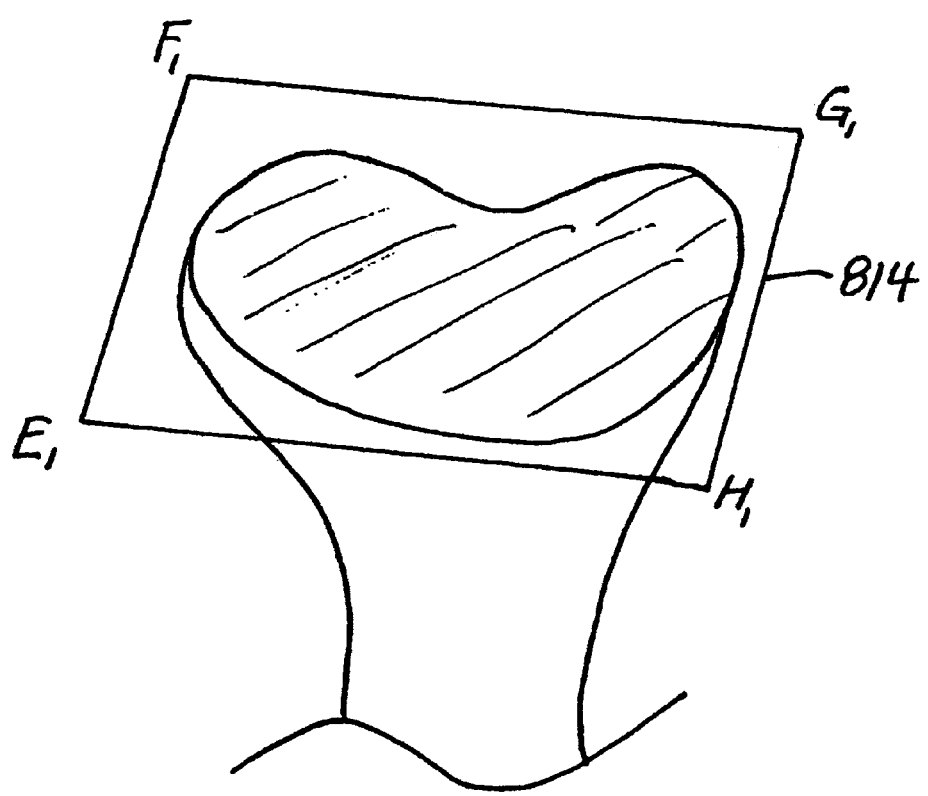

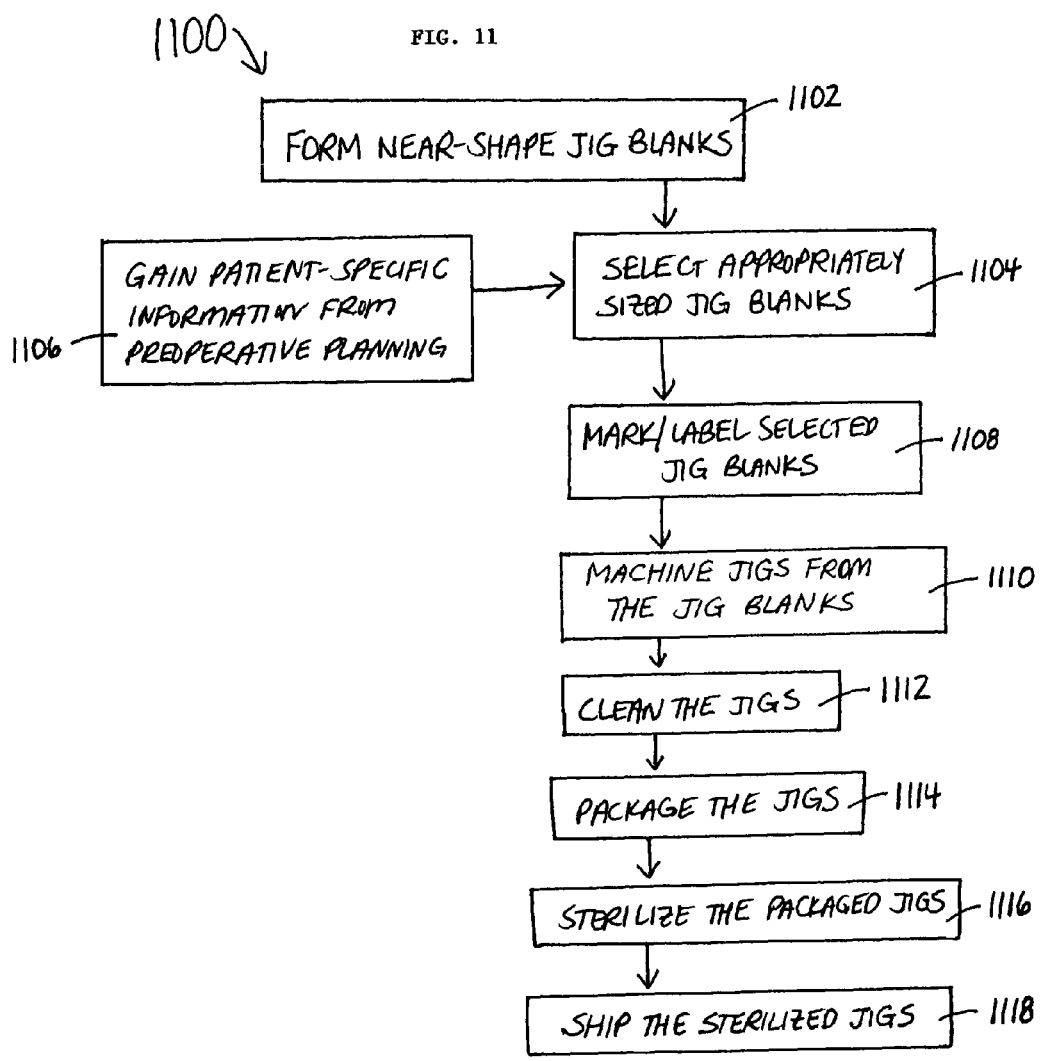

FIG. 22
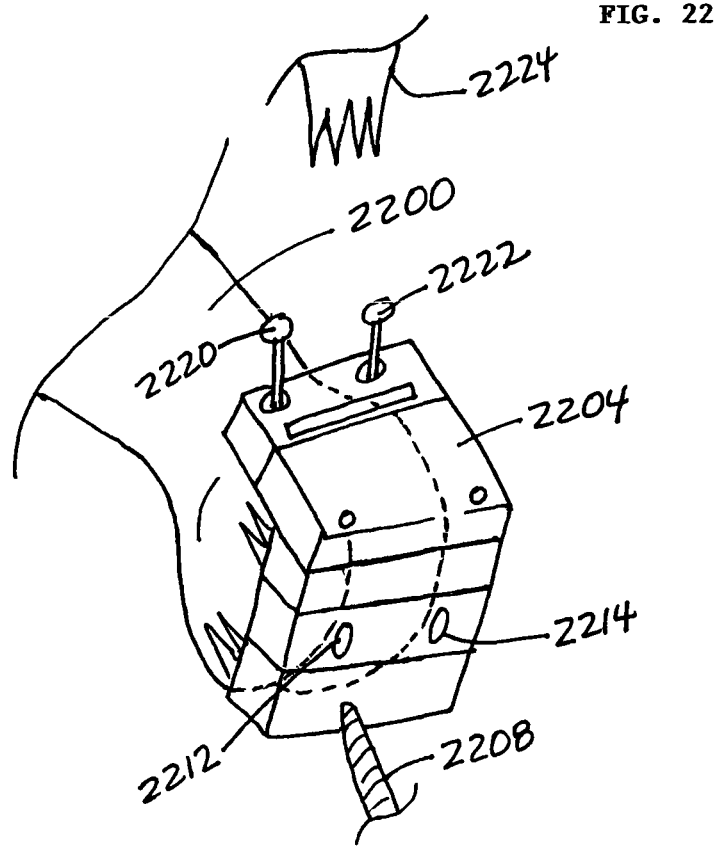
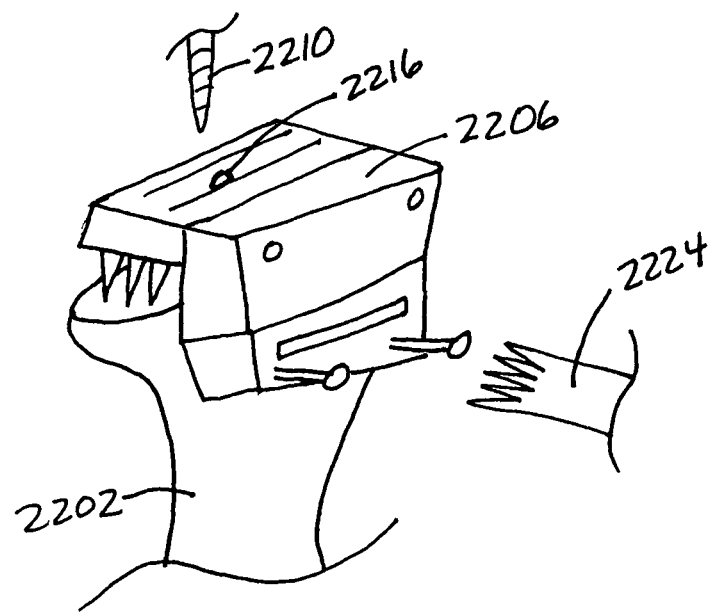

ARTHROPLASTY DEVICES AND RELATED METHODS

CROSS-REFERENCE TO RELATED APPLICATIONS

This application claims the benefit of priority, under 35 U.S.C. §119(e), to U.S. Pat. Appl. Ser. No. 60/773,491, filed on Feb. 15, 2006, and U.S. Pat. Appl. Ser. No. 60/780,757, filed on Mar. 9, 2006, both of which are hereby incorporated by reference in their entirety.

TECHNICAL FIELD

The methods and apparatuses described herein relate generally to the field of implants, as well as jigs that may be used to assist in positioning implants at a target site. More specifically, the methods and apparatuses described herein relate to the field of arthroplasty jigs, including the production of arthroplasty jigs and the alignment of arthroplasty jigs at a target site.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty (TKA), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

Preoperative planning may be used prior to some TKA procedures to help determine where to position an implant and how to align the implant. Certain preoperative planning methods may include making these determinations based on a two-dimensional image of the target site. In some cases, though, the two-dimensional image may not provide sufficient guidance for precisely replacing a patient's diseased knee with an implant. For example, a physician may rely on certain landmarks of the target site, as shown in the two-dimensional image, for determining placement of an implant. Examples of knee region landmarks that may be relatively easily viewed in a two-dimensional image include the medial and lateral epicondyles of the distal region of the femur. However, the corresponding bone regions in the body typically are covered with soft tissue. This soft tissue may cause the landmarks to be partially obscured or completely hidden when the physician is trying to position an implant at the target site, and may make it especially difficult to view the landmarks when the physician is using a relatively small incision. Moreover, using such landmarks to position an implant at a target site may have added difficulty in that the locations and sizes of the landmarks can vary greatly from one patient to another. As a result, a landmark-based technique that is used for one patient may not be suitable for use with another patient. For at least the reasons provided above, a physician using a landmark-based approach may experience difficulty during surgery, such as difficulty in accessing the rotational axis. Because of this difficulty, many surgeons opt to rely significantly on their intuition and previous experience to guide them in a TKA procedure. The result can be inconsistent surgical outcomes, given the highly complex nature of the human knee, with its six degrees of freedom and features, such as dimensions and alignment, that can vary greatly from one patient to the next.

In certain TKA surgeries, a robot is employed to machine the distal region of the femur and/or the proximal region of the tibia based on, for example, image-based preoperative planning. The robot may form cavities that may be used for attachment of prosthetic implants. While robot-assisted TKA procedures may be successful in terms of accuracy of alignment, they can require relatively long incisions and result in relatively long surgery times. Furthermore, the cost of a robot-assisted TKA procedure, including the capital cost, can be relatively high (e.g., two to three times the cost of a traditional TKA procedure).

In some TKA surgeries, an imageless navigation system is employed, in which planning is done intraoperatively (i.e., during the operation), without the use of preoperative radiographic images. The navigation system can assist surgeons in positioning prosthetic implants, and may thereby enhance the longevity of the implants. However, the navigation system may not provide information regarding the optimal alignment of an implant. Furthermore, the capital equipment cost associated with a navigation system can be relatively high, and the use of a navigation system may result in a longer incision, a higher surgical cost, and a longer duration of surgery, as compared to traditional surgery.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant. However, prior to treating any regions of a bone, it is important to correctly determine the location at which the treatment will take place. In some methods, an arthroplasty jig may be used to accurately position a finishing instrument, such as a cutting, drilling, reaming, or resurfacing instrument. The arthroplasty jig may, for example, include one or more apertures and/or slots that are configured to accept such an instrument.

A relatively high number of arthroplasty procedures are performed every year in the United States, and throughout the rest of the world. More specifically, in the United States alone, more than 300,000 people underwent TKA surgeries in 2005. By 2008, it is expected that approximately 1,000,000 people per year across the globe will have a TKA surgery. Accordingly, it would be desirable to improve the success rate of arthroplasty procedures, in terms of both efficiency and effectiveness. It would also be desirable to be able to meet demand for arthroplasty devices by manufacturing arthroplasty jigs and/or implants, including customized arthroplasty jigs and/or implants, relatively efficiently.

BRIEF SUMMARY

Described here are methods and devices that may be used to efficiently manufacture arthroplasty jigs configured for use at specific target sites, as well as methods and devices that may be used to enhance the positioning and alignment of an arthroplasty jig at a target site. The methods and devices described here include certain features that may enhance the customization of an arthroplasty procedure, and may thereby result in reduced procedure time and recovery time, as well as a reduced likelihood of complications.

Some of the methods described here comprise forming an arthroplasty jig, such as a knee arthroplasty jig. In some variations of the methods, the arthroplasty jig may be formed from a near-shape arthroplasty jig blank having at least one feature specific to a target site to be matched by the arthroplasty jig. In certain variations of the methods, the arthroplasty jig may have a first configuration, and may be formed from a near-shape arthroplasty jig blank having a second configuration approximating the first configuration.

Arthroplasty jig blanks, and methods of forming arthroplasty jig blanks, are also described herein. Some of the arthroplasty jig blanks comprise a jig blank body, are configured to be formed into an arthroplasty jig, and have at least one feature specific to a target site to be matched by the arthroplasty jig. Certain of the methods comprise forming a near-shape arthroplasty jig blank that is configured to be formed into an arthroplasty jig, and that has at least one feature specific to a target site to be matched by the arthroplasty jig.

The target site to be matched by the arthroplasty jig may be, for example, a left knee or a right knee, and/or may be a valgus knee, a varus knee, or a neutral knee. In some variations, the target site to be matched by the arthroplasty jig may be a femur. In certain variations, the target site to be matched by the arthroplasty jig may be a tibia.

The arthroplasty jig that is formed from the near-shape arthroplasty jig blank may be a customized arthroplasty jig, and/or may be a femoral arthroplasty jig or a tibial arthroplasty jig. In some variations, the method may comprise adding at least one patient-specific feature, such as a cavity, to the near-shape arthroplasty jig blank to form the arthroplasty jig. The patient-specific feature may be added to the near-shape arthroplasty jig blank using, for example, a milling process. In certain variations, forming the arthroplasty jig from the near-shape arthroplasty jig blank may comprise machining the near-shape arthroplasty jig blank.

Some of the methods may comprise forming a plurality of near-shape arthroplasty jig blanks that are configured to be formed into an arthroplasty jig, and that have at least one feature specific to a target site to be matched by the arthroplasty jig. In certain variations of the methods, one or more near-shape arthroplasty jig blanks may be formed using injection-molding technology.

Surface-matching devices, which may be used to position an arthroplasty jig at a target site in a body of a subject, also are described herein, along with related methods. Some of the surface-matching devices comprise at least one block and at least one pin extending from a portion of the block, and are configured to position an arthroplasty jig at a target site in a body of a subject. Certain of the methods comprise positioning a surface-matching device at a target site in a body of a subject, where the surface-matching device comprises at least one block and at least one pin extending from a portion of the block, and the surface-matching device is configured to position an arthroplasty jig at a target site in a body of a subject.

Some variations of the surface-matching devices may comprise a plurality of pins. One or more of the pins of a surface-matching device may have an end that is configured to contact at least one of bone and cartilage when the surface-matching device is positioned at a target site in a body of a subject. The surface-matching devices may be configured to position an arthroplasty jig, such as a knee arthroplasty jig, at a target site in a knee of a subject.

BRIEF DESCRIPTION OF THE DRAWINGS

FIG. 3 is a flowchart representation of a method of designing and manufacturing arthroplasty jigs.

FIG. 6A is a front view of a three-dimensional model of a distal portion of a femur of a subject.

FIG. 6B is a side view of the model of FIG. 6A.

FIG. 6C is a front view of a femoral implant.

FIG. 6D is a side view of the femoral implant of FIG. 6C.

FIG. 6E is a perspective view of a femoral implant and a distal portion of a femur of a subject.

FIGS. 8D and 8E illustrate a shape-fitting method for a tibial implant.

FIG. 11 is a flowchart representation of a method for forming arthroplasty jigs.

FIG. 22 is a perspective view of arthroplasty jig instruments being placed on a distal portion of a femur of a subject and a proximal portion of a tibia of a subject, using multi-pin guided devices.

DETAILED DESCRIPTION

Described here are arthroplasty jigs, and methods of making and using arthroplasty jigs, having features that may provide for enhanced alignment and positioning of the arthroplasty jigs at a target site. Certain of the methods described here comprise forming arthroplasty jigs from near-shape arthroplasty jig blanks having at least one feature specific to a target site to be matched by the arthroplasty jigs. Because the near-shape arthroplasty jig blanks already have one or more features directed to the configuration of the target site, they may be used to form arthroplasty jigs relatively efficiently. Also described here are devices that may be used to enhance the alignment and positioning of an arthroplasty jig at a target site. This enhanced arthroplasty jig alignment and positioning may, in turn, result in enhanced implant alignment and positioning at the target site. As the alignment and positioning of an implant are improved, the result may be a decreased likelihood of follow-up surgery (e.g., to adjust the alignment of the implant), and/or an increase in the useful life of the implant. Additional results may include reduced procedure time and fewer complications during and/or after surgery. Moreover, fewer resections and/or holes may be made when an arthroplasty jig is properly positioned and aligned at a target site. It should be understood from the outset that while knee arthroplasty jigs are described in detail here, one or more of the features or methods described here may be employed with other types of arthroplasty jigs, such as arthroplasty jigs that are suited for use in the hip, shoulder, elbow, etc.

Figure 1A:
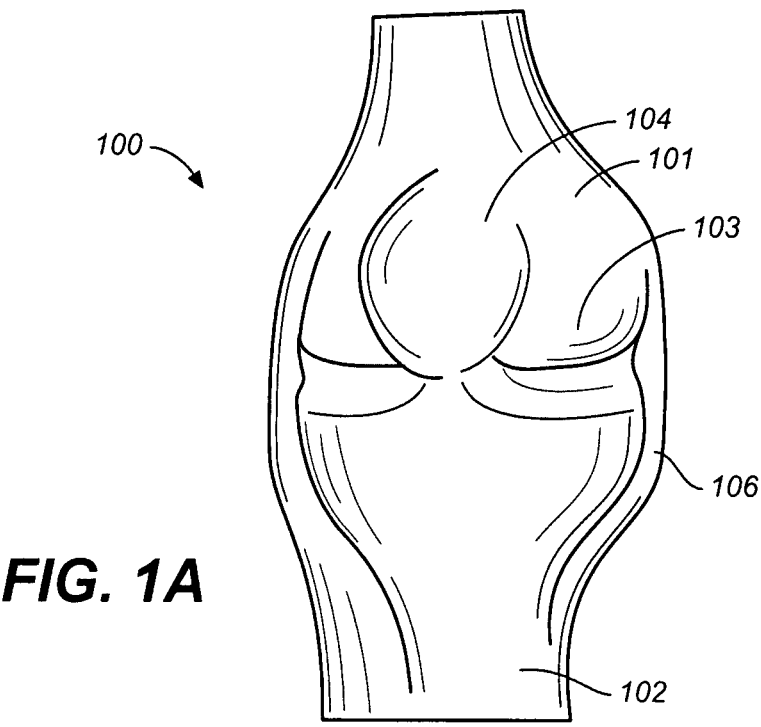
FIG. 1A is an illustrative view of a knee of a subject in extension.
Figure 1B:
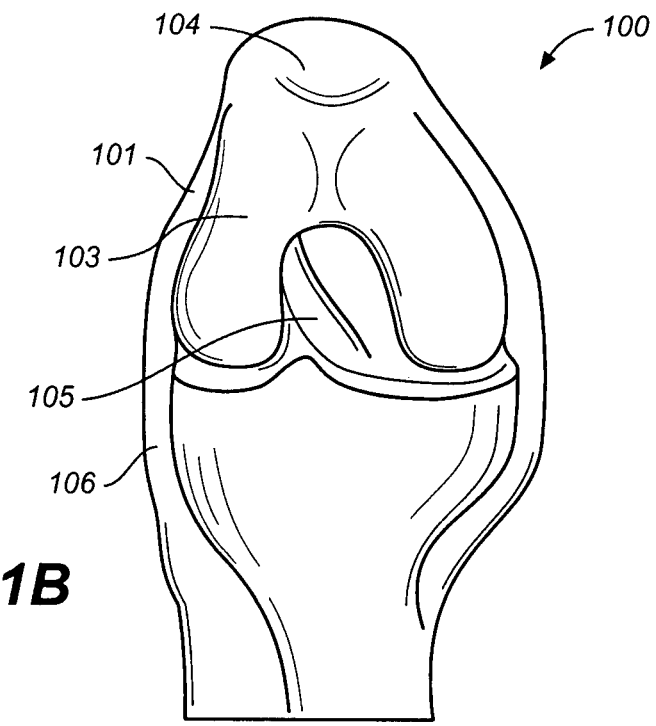
FIG. 1B is an illustrative view of the knee of FIG. 1A in flexion.

Turning now to the figures, FIG. 1A shows a knee (100) of a subject in extension, and FIG. 1B shows knee (100) in flexion. Knee (100) is located at the juncture between the distal end of a femur (101) and the proximal end of a tibia (102). All human knees share certain anatomical features, including articular cartilage (103), a patella (104), an anterior cruciate ligament or ACL (105), and collateral ligaments (106). However, the dimensions of these features are not identical from one person to the next. Furthermore, alignment can vary among different people. For example, one person may have a valgus knee, while another person may have a varus knee, and a third person may have a neutral knee. As a result of these and other variations, the positioning and alignment of a knee implant can be different for different people. Thus, in order to ensure longevity of a knee implant, the implant should be positioned with high translational and rotational accuracy.

In some variations of an arthroplasty procedure, one or more arthroplasty jigs may be employed to help prepare the damaged region for an implant, and to increase the likelihood that the implant will be correctly positioned and aligned at a target site in the damaged region. The arthroplasty jigs may be used, for example, to aid in the correct placement of finishing instruments, such as cutting, drilling, reaming, and resurfacing instruments. As an example, some arthroplasty methods may include using an arthroplasty jig to accurately position a reciprocating saw blade. The reciprocating saw blade may be used, for example, to cut the damaged bone region to provide one or more planar surfaces. The planar surfaces may assist in the alignment and positioning of an implant at a target site in the damaged bone region. Arthroplasty jigs may also be used, for example, to position one or more pins that secure an implant to a target site in the damaged bone region.

In some variations, an arthroplasty jig may help to position finishing instruments that are used to form a relatively high number of cuts and/or apertures in a damaged bone region. For example, arthroplasty jigs may be used during a TKA procedure to form at least ten resections in a damaged knee region that allow implants to be attached to a distal region of the femur and a proximal region of the tibia.

Figure 2:
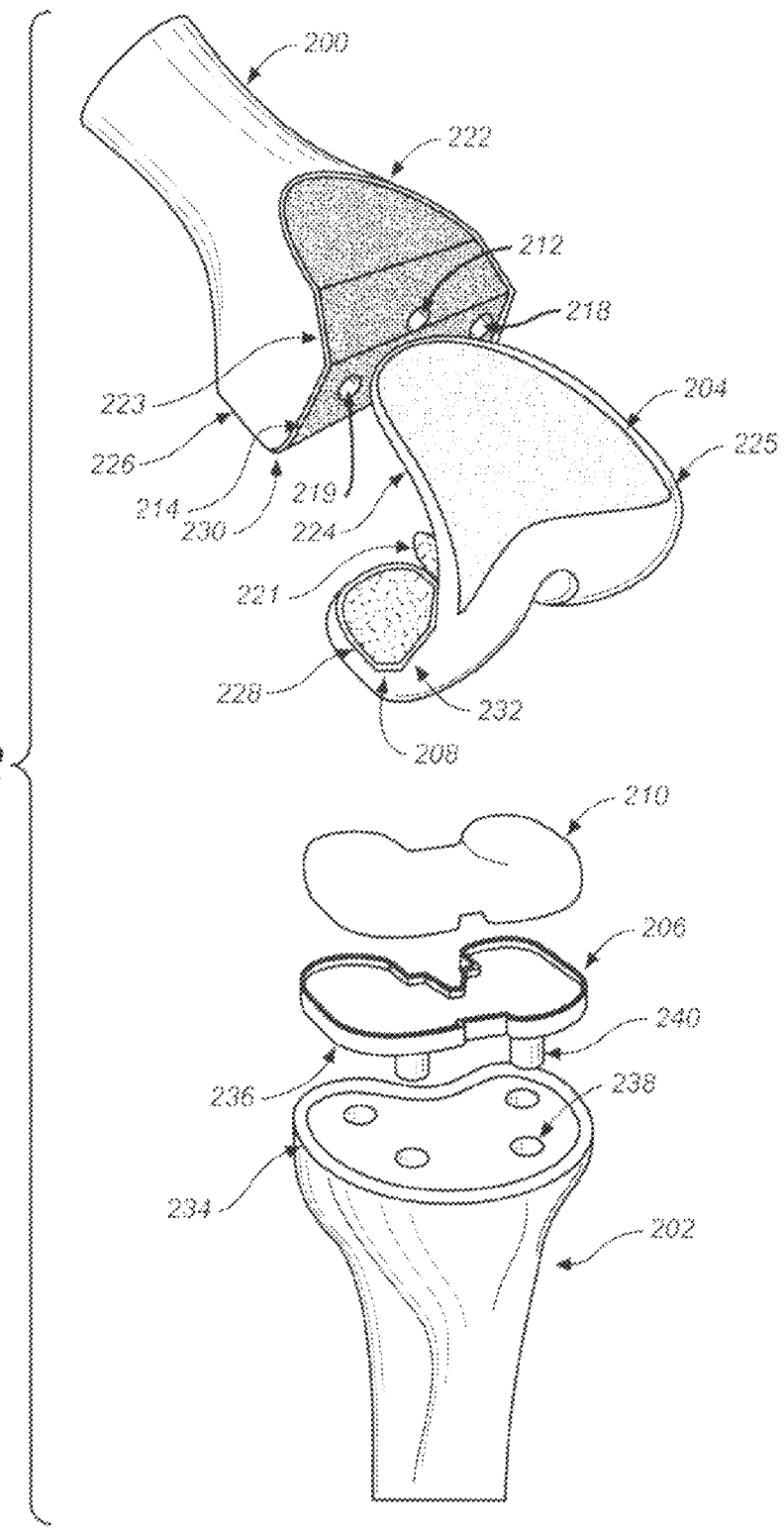
FIG. 2 is a perspective view of femoral and tibial osteotomies and implants.

FIG. 2 illustrates exemplary osteotomy cuts that may generally be formed on the distal region of a femur (200) and the proximal region of a tibia (202), using one or more arthroplasty jigs. The cuts are used to help attach or press-fit a femoral implant (204) to femur (200), and a tibial implant (206) to tibia (202). Femoral implant (204) includes a load-bearing component (208), and tibial implant (206) includes a load-bearing component (210). The load-bearing components of the implants may be formed of, for example, one or more plastics. Examples of processes that may be conducted to provide the osteotomy cuts include the following: intermedullary drilling to enter a femoral medullary canal (212); forming a distal femoral resection (214) that is configured to mate with femoral load-bearing plastic component (208); drilling a right femoral stem hole (218) that is configured to mate with a right stem (220) of femoral implant (204) (which is located on a side of femoral implant (204) that is not shown); drilling a left femoral stem hole (219) that is configured to mate with a left stem (221) of femoral implant (204); forming an anterior femoral resection (222) that is configured to mate with a planar surface (224) of femoral implant (204); forming an anterior femoral chamfer resection (223) that is configured to mate with a planar surface (225) of the femoral prosthetic implant; forming a posterior femoral resection (226) that is configured to mate with a planar surface (228) of femoral implant (204); forming a posterior femoral chamfer resection (230) that is configured to mate with a planar surface (232) of femoral implant (204); forming a tibial resection (234) that is configured to mate with a planar surface (236) of tibial implant (206); and forming a tibial stem feature punch (238) that is configured to mate with a feature (240) of tibial implant (206).

The cuts and holes described above with reference to FIG. 2 are illustrative, and are not meant to be limiting. A process of preparing a bone region for one or more implants may include forming more cuts and/or holes than described above, or fewer cuts and/or holes than described above. Furthermore, different combinations of cuts, holes, grooves, ridges, etc. may be used. Examples of instruments that may be used to prepare a target site for an implant include distal resectors, anterior-posterior (AP) sizers, sliding 4-in-1 cut blocks, tibial resectors, offset tibial templates and punch towers, femoral impactors, handles/styluses, etc.

In certain variations, an arthroplasty jig may be customized to correspond to a particular patient's anatomy. As described above, while individual human knees share some characteristics, they also can differ from each other in certain ways, such as alignment. The use of a customized arthroplasty jig may enhance the precision of any cuts or other modifications that are made to a damaged region, such as a damaged knee region, during surgery to repair or restore the damaged region. For at least these reasons, customized arthroplasty jigs can provide for an effective and efficient arthroplasty procedure.

FIG. 3 is a flowchart representation of a method (300) for forming and using customized arthroplasty jigs using preoperative planning. The preoperative planning portion (302) of the method is an attempt to best determine the parameters and features of a target site prior to surgery, so that the positioning and alignment of one or more implants at the target site during surgery can be optimized.

As shown in FIG. 3, preoperative planning portion (302), described with reference to a knee arthroplasty, proceeds as follows. First, after a patient has undergone magnetic resonance imaging (MRI), computed tomography (CT), and/or one or more other medical imaging processes, the patient's imaging data is sent to a preoperative planning computer program. Upon receipt of the data, the computer program converts the data (e.g., two-dimensional MRI images) into three-dimensional anatomical computer models of the knee joint (304) with the aid of a medical imaging conversion computer program. For example, current commercially available MRI machines use 8 bit (255 grayscale) to show the human anatomy. Therefore, certain components of the knee, such as the cartilage, cortical bone, cancellous bone, meniscus, etc., can be uniquely viewed and recognized with 255 grayscale. The specialized medical converging software recognizes the anatomy of the knee and shapes the knee using mathematical algorithms, such as sequences of $n^{th}$ order polynomials, where $n \geq 3$. A technique such as surface-rendering is then used to construct a three-dimensional model of the knee joint. Examples of medical imaging computer programs that may be used here include Analyze (from AnalyzeDirect, Inc., Overland Park, Kans.), open-source software such as the Insight Toolkit (ITK, www.itk.org) and 3D Slicer (www.slicer.org), and Mimics (from Materialise, Ann Arbor, Mich.). The resulting three-dimensional anatomical computer models of the knee joint include the cortical bone of the femur and the tibia, as well as articular cartilage attached to the distal region of the femur and the proximal region of the tibia. The computer program typically automatically excludes the rest of the soft tissue, as well as the cancellous bone, from the three-dimensional computer models, although in some variations the computer program may not automatically exclude the rest of the soft tissue and/or the cancellous bone.

Once the three-dimensional computer models of the knee have been formed, the appropriately sized knee implants (here, femoral and tibial implants) are selected (306). This selection process may be accomplished with the aid of a computer program including one or more selection algorithms. Example of suitable computer programs include SolidWorks® software (from SolidWorks Corp., Concord, Mass.), and Pro/Engineer and Pro/Mechanica (both from Parametric Technology Corp.). These computer programs are only exemplary computer programs, and one or more other computer programs may be used as appropriate. In some variations, the process of selecting the appropriately sized knee implants may be conducted by one or more surgeons, bioengineers, other qualified medical professionals, etc., by using a computer graphic method to compare the critical dimensions of the implant computer models to those of the three-dimensional computer models of the knee. Critical dimensions that may be compared include, for example, the anterior-posterior (A-P) extent inequality constraint, the medial-lateral (M-L) extent inequality constraint, and the lateral condyle radii inequality constraint. Other critical dimensions may alternatively or additionally be employed. In some variations, one or more of the above-described computer software programs may be used in comparing an implant computer model to a knee computer model.

After the implant selection process has been completed, a shape-fitting (also known as surface-matching) process is performed (308). The shape-fitting process may be conducted with the aid of a computer program employing one or more shape-fitting algorithms. For example, shape-fitting between a patient's condyle surface and an implant's condyle surface may be accomplished using any of a number of different methods, including but not limited to point-to-point optimization and normal surface vector-to-vector optimization. Alternatively or additionally, the shape-fitting process may be conducted by one or more surgeons, bioengineers, other qualified medical professionals, etc., using a computer graphic method that includes superimposing different implant computer models onto the three-dimensional computer models of the knee. Examples of computer software that may be used to achieve this shape-fitting process include SolidWorks® software (from SolidWorks Corp., Concord, Mass.), and Pro/Engineer and Pro/Mechanica (both from Parametric Technology Corp.). The surgeon can then evaluate whether the implant sizes have been properly selected (310). If not, then the process is repeated, starting with implant selection (306). If the selected implants are of appropriate sizes, however, then the preoperative planning portion of the method is complete.

The data gathered from preoperative planning is then sent to the hospital for surgical preparation (312), and to an arthroplasty jig manufacturer for production of one or more customized arthroplasty jigs (314). In some variations of the method, only one of these steps may be performed, while in other variations of the method, both of these steps may be performed. The hospital, upon receiving the preoperative planning data, can prepare the required sets of surgical instruments, keeping the selected implant sizes in mind. The arthroplasty jig manufacturer can use the preoperative planning data to fabricate a customized arthroplasty jig (e.g., a single-use arthroplasty jig) for use in surgery. After the appropriate preparation has taken place, the instrumentation and the arthroplasty jig or jigs are sent to an operating room (316), where an arthroplasty surgical procedure is conducted.

Figure 4A:
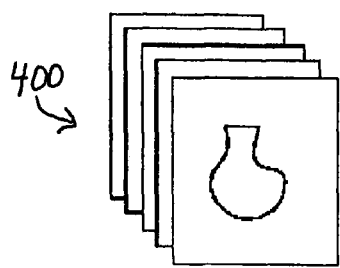
FIG. 4A is an illustration of two-dimensional images of multiple segmentations of a femur of a subject.

As described above, during a preoperative planning process, three-dimensional computer models of a knee region may be formed from one or more two-dimensional images of the knee region. FIG. 4A shows multiple two-dimensional anatomical images (400) of a distal femur region of a knee taken using, for example, MRI or CT technology, or another imaging technology. A three-dimensional model (402) of the distal femoral region, shown in FIG. 4B, may be reconstructed based on the multiple two-dimensional images of FIG. 4A. Similarly, FIG. 5A shows multiple two-dimensional anatomical images (500) of a proximal tibial region of a knee, and FIG. 5B shows a three-dimensional model (502) of the proximal tibial region, which may be reconstructed based on the images of FIG. 5A.

Figure 4B:
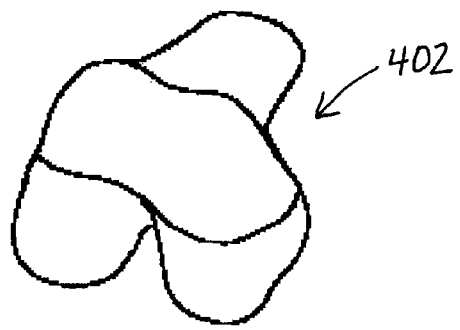
FIG. 4B is a three-dimensional anatomical computer model of a distal portion of a femur formed from the images of FIG. 4A.
Figure 5A:
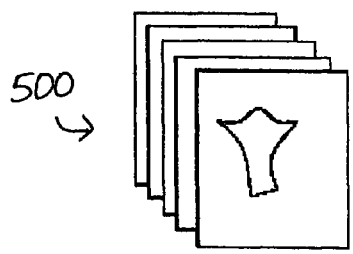
FIG. 5A is an illustration of two-dimensional images of multiple segmentations of a tibia of a subject.
Figure 5B:
FIG. 5B is a three-dimensional anatomical computer model of a distal portion of a tibia formed from the images of FIG. 5A.

The three-dimensional models of FIGS. 4B and 5B above may be obtained using either a surface rendering technique or a volume rendering technique. Surface rendering is an imaging technique that starts with a process such as iso-surfacing, iso-contouring, surface extraction, or border-following. After this process is complete, three-dimensional models having polygon meshes are constructed for display using, for example, conventional geometric rendering techniques. Volume rendering is an imaging technique for visualizing three-dimensional arrays (which are widely used for representing image information) of sampled two-dimensional data. Using either of the above-described surface or volume rendering techniques, cortical bone and articular cartilage of the femur and the tibia are extracted to construct three-dimensional models of these regions while filtering out other anatomy. Surface rendering techniques and volume rendering techniques are described, for example, in Foley et al., *Computer Graphics: Principles and Practice* (Addison Wesley, 1990); Glassner, *Principles of Digital Image Synthesis* (Morgan Kaufmann, 1995); Pharr et al., *Physically Based Rendering* (Morgan Kaufmann, 2004); Dutre et al., *Advanced Global Illumination*, (AK Peters, 2002); Jensen, *Realistic Image Synthesis Using Photon Mapping* (AK Peters, 2001); Shirley et al., *Realistic Ray Tracing* (AK Peters, 2nd ed., 2003); Glassner, *An Introduction to Ray Tracing* (Academic Press, 1989); Cohen et al., *Radiosity and Realistic Image Synthesis* (AP Professional, 1993); Akenine-Moller et al., *Real-Time Rendering* (AK Peters, 2nd ed., 2002); Gooch et al., *Non-Photorealistic Rendering* (AK Peters, 2001); Strothotte et al., *Non-Photorealistic Computer Graphics* (Morgan Kaufmann, 2002); and Blinn, *Jim Blinn's Corner—A Trip Down the Graphics Pipeline* (Morgan Kaufmann, 1996), all of which are hereby incorporated by reference in their entirety.

FIGS. 6A and 6B show front and side views, respectively, of a three-dimensional model of the distal region of a femur (600), and FIGS. 6C and 6D show front and side views, respectively, of a three-dimensional model of a corresponding femoral implant (602). Based on a coordinate system (604) (shown in FIG. 6A), a point $A(x_1,y_1)$ is defined where $dx/dy=0$ on the boundary curve represented by $x=f_1(y)$ (which represents the medial/lateral epicondyle shape). Similarly, a point $B(x_2,y_2)$ is defined where $dx/dy=0$ on the boundary curve represented by $x=f_2(y)$ (which represents the lateral/medial epicondyle shape). Line (AB), which connects point A to point B, is referred to as the transepicondyle axis. Additionally, a point $C(x_3,y_3)$ is defined where $dy/dx=0$ on the curve represented by $y=g_1(x)$, and a point $D(x_4,y_4)$ is defined where $dy/dx=0$ on the curve represented by $y=g_2(x)$. Line (CD), which connects point C to point D, is referred to as the anterior-posterior axis, or the AP axis. Length (L1) of line (AB) is referred to as the M-L extent, and length (L2) (shown in FIG. 6B) is referred to as the A-P extent. The M-L and A-P extents provide information that may be used in selecting an appropriately sized femoral implant. The corresponding implant dimensions (D1) and (D2), shown in FIGS. 6C and 6D, respectively, typically should closely match with, or be less than, lengths (L1) and (L2), respectively.

FIG. 6E is a perspective view of three-dimensional computer models of the distal region of femur (600) and the corresponding femoral implant (602). Once the appropriate femoral implant size has been determined, the transepicondyle axis (line (AB)) and the AP axis (line (CD)) can be referenced to provide initial translational and rotational positions along the x-, y-, and z-axes (shown in a coordinate system (606)) of femoral implant (602). Moreover, the surface profiles of the condyles, represented by the functions $y=h_1(x)$ and $y=h_2(x)$, and the corresponding implant surface profiles of the condyles, represented by $y=h_3(x)$ and $y=h_4(x)$, are closely superposed to provide final translational and rotational positions of the femoral implant with respect to the three-dimensional computer model of the distal region of femur (600).

Figure 7A:
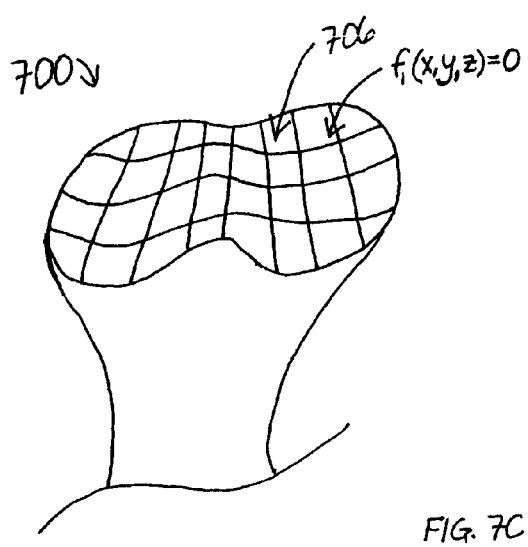
FIG. 7A is a perspective view of a three-dimensional computer model of a proximal portion of a tibia of a subject.
Figure 7B:
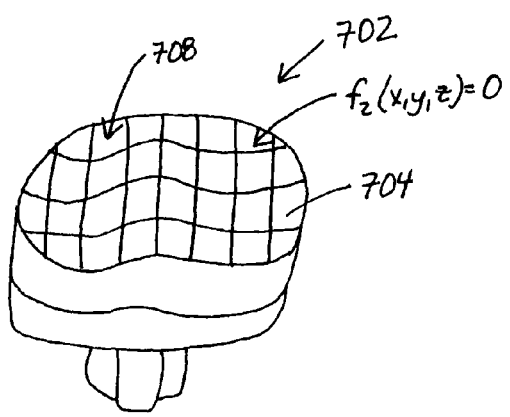
FIG. 7B is a side view of a tibial implant including a load-bearing component.
Figure 7C:
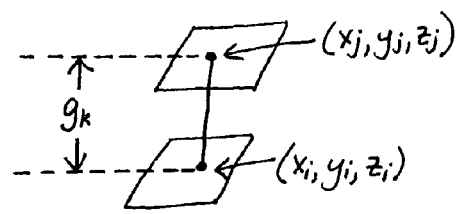
FIG. 7C illustrates a shape-fitting method.

FIGS. 7A and 7B are perspective views of three-dimensional computer models of the proximal region of a tibia (700) and a corresponding tibial implant (702) including a load-bearing component (704). The articular surface of the tibial plateau (706) on tibia (700) is represented by the function $f_1(x,y,z)=0$, and the load-bearing surface (708) on tibial implant (702) is represented by the function $f_2(x,y,z)=0$, based on an x,y,z-coordinate system. A computer can be used to surface match the tibial plateau surface to the load-bearing surface by superposing the two functions. Additionally, the $k^{th}$ distance $(g_k)$ between the normal vector on the surface element of the tibial surface at $(x_i,y_i,z_i)$ and the corresponding point $(x_j,y_j,z_j)$ on the implant-bearing surface is measured as shown in FIG. 7C. The optimal surface matching is achieved when the minimum value J=MINIMUM (SUM (from 1 to k) $(g_k\hat{\ }2)\hat{\ }(1/26)$).

Figure 8A:
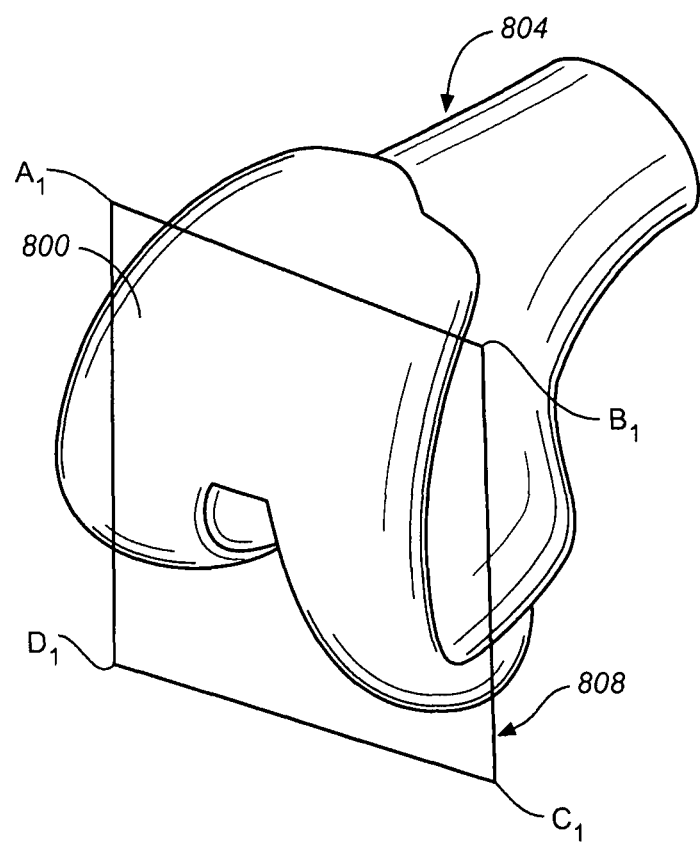
FIGS. 8A and 8B illustrate a shape-fitting method for a femoral implant.
Figure 8B:
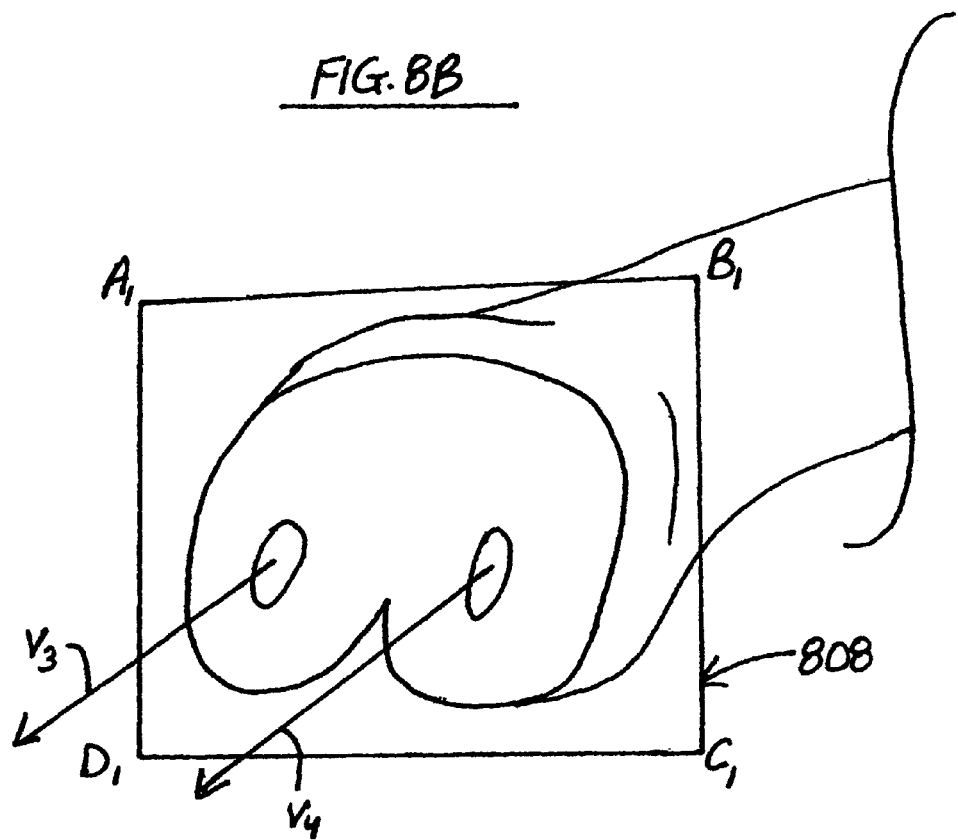
Figure 8C:
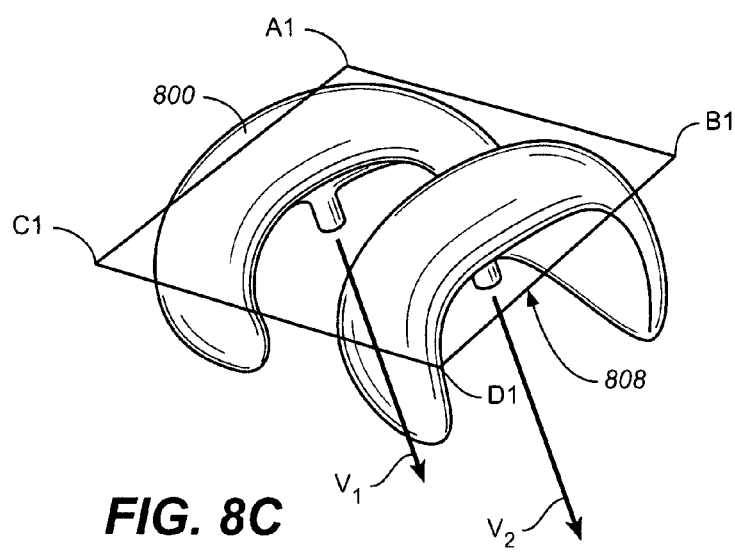
FIG. 8C is a perspective view of the femoral implant of FIG. 8A.
Figure 8D:
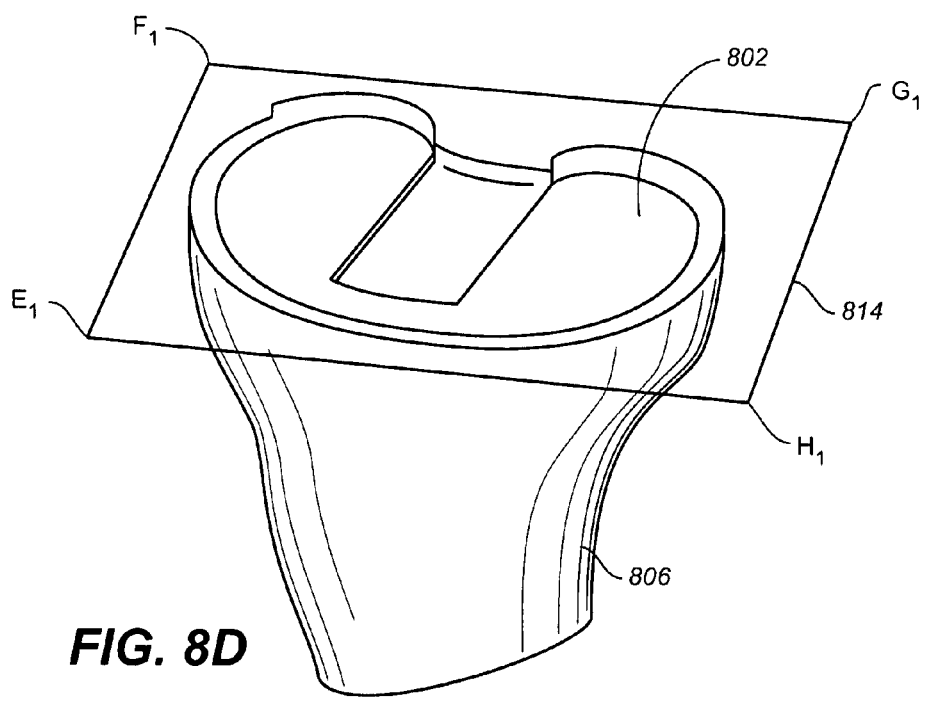

FIGS. 8A and 8D are graphical representations of a femoral implant (800) being shape fitted onto a distal region of a femur (804), and a tibial implant (802) being shape fitted onto a proximal region of a tibia (806), respectively. This preoperative shape fitting may, for example, result in optimal knee joint motion after a TKA procedure. After the positions of femoral implant (800) and tibial implant (802) have been set graphically, the distal femoral cut plane (808) formed from points $A_1$, $B_1$, $C_1$, and $D_1$ (shown in FIGS. 8A-8C), as well as the two drill hole directions $(v_1)$ and $(v_2)$ (shown in FIG. 8C), are determined. Additionally, the proximal tibial cut plane (814) formed from points $E_1$, $F_1$, $G_1$, and $H_1$ (shown in FIGS. 8D and 8E) is determined. This information may then be incorporated into the femoral and tibial arthroplasty jig designs. More specifically, distal femoral cut plane (808) is incorporated into the jig design for a femoral arthroplasty jig, and the stem hole direction vectors $(v_3)$ and $(v_4)$ (shown in FIG. 8B) also are determined. Furthermore, proximal tibial cut plane (814), which is determined by the shape-fitting method, is incorporated into the jig design for a tibial arthroplasty jig. This procedure can be automatically incorporated into a computer program without the manual use of a graphical interface.

As described above, customized arthroplasty jigs may be formed using three-dimensional computer models. The arthroplasty jigs may be manufactured using any of a number of different methods, including rapid production methods such as computer numerical control (CNC) machining, stereolithography apparatus (SLA) methods, and/or one or more other rapid prototyping technologies.

Figure 9A:
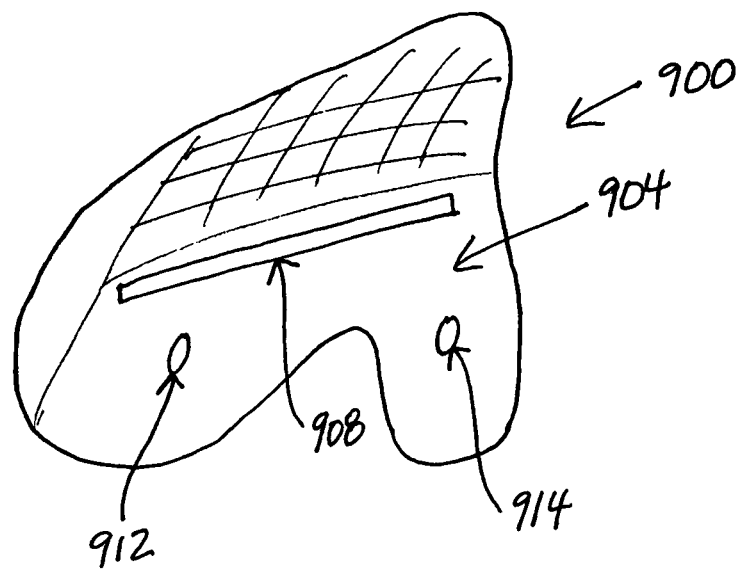
FIG. 9A is a perspective view of a femoral arthroplasty jig.
Figure 9B:
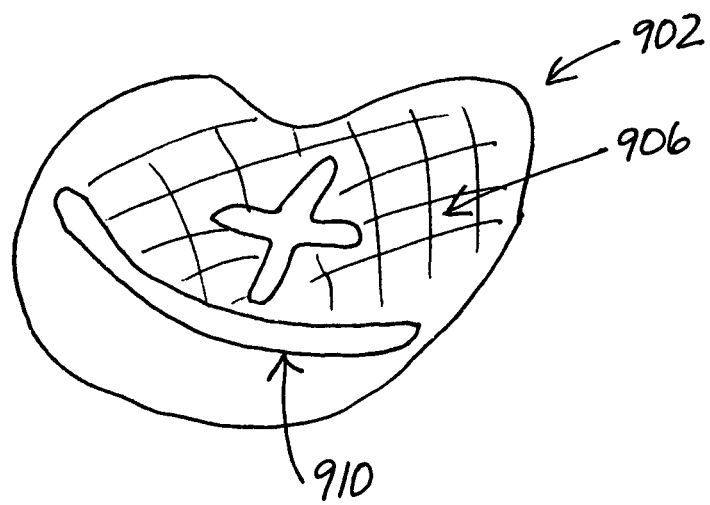
FIG. 9B is a perspective view of a tibial arthroplasty jig.

Examples of arthroplasty jigs are provided in FIGS. 9A and 9B. FIG. 9A shows a femoral arthroplasty jig (900), and FIG. 9B shows a tibial arthroplasty jig (902). Femoral arthroplasty jig (900) has an interior matching surface (904), and tibial arthroplasty jig (902) has an interior matching surface (906). Interior matching surfaces (904) and (906) may be created based on three-dimensional computer models of the femur and the tibia, such as the three-dimensional computer models described above. When the interior matching surfaces are created from these three-dimensional computer models, they may have shapes and/or cavities including damaged bone and articular cartilage. These shapes and/or cavities may eventually allow the arthroplasty jigs to form a precise match, during arthroplasty surgery, with the distal region of the corresponding femur and the proximal region of the corresponding tibia. Interior surfaces (904) and (906) thus may serve as reference surfaces for mechanical registration to precisely position saw guiding slots (908) and (910) for the femoral distal and tibial planes, and drill holes (912) and (914) for stem holes on the arthroplasty jigs. Once arthroplasty jigs have been formed based on three-dimensional computer models, the arthroplasty jigs may be packaged, sterilized, and shipped to a designated hospital.

Figure 10:
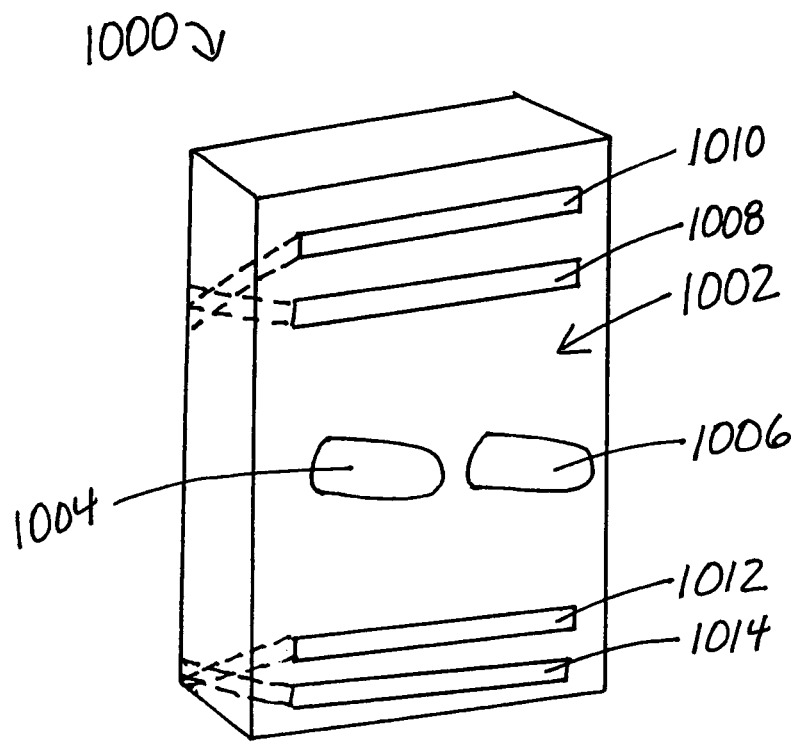
FIG. 10 is a perspective view of a femoral cutting jig.

In some variations, an arthroplasty jig may be designed, based on implant size, to assist with anterior, anterior chamfer, posterior, and posterior chamfer cuts. An example of such an arthroplasty jig is shown in FIG. 10. As shown in FIG. 10, an arthroplasty jig (1000) has a flat surface (1002) and two stems (1004) and (1006), corresponding to the femoral distal cut plane and two drill holes, respectively. Arthroplasty jig (1000) also includes four saw-guiding slots: an anterior cut slot (1008), an anterior chamfer cut slot (1010), a posterior cut slot (1012), and a posterior chamfer cut slot (1014). While the dimensions of arthroplasty jig (1000) may not be patient-specific, they may be determined according to the size of a selected femoral implant. This implant size information may be sent to the surgeon in advance, so that the surgeon can prepare all of the necessary instrumentation prior to the surgery.

In some variations, methods for forming arthroplasty jigs may include using near-shape arthroplasty jig blanks. In other words, the arthroplasty jig blanks may be pre-designed to include certain features that are shared by certain patients. For example, a near-shape arthroplasty jig blank may be designed to be used to form an arthroplasty jig for a subject having a valgus knee. Advantageously, near-shape arthroplasty jig blanks may be mass-produced, and thereafter, individual near-shape arthroplasty jig blanks may be customized for a specific patient. The fact that the near-shape arthroplasty jig blanks already incorporate certain features that will be retained in the arthroplasty jigs may allow the near-shape arthroplasty jig blanks to be used to produce customized arthroplasty jigs relatively rapidly.

FIG. 11 is a flowchart representation of a method (1100) for forming customized arthroplasty jigs, such as single-use arthroplasty jigs, using near-shape arthroplasty jig blanks. First, near-shape femoral and/or tibial arthroplasty jig blanks are formed using one or more injection molding techniques, thermal plastic press forming techniques, and/or other plastic forming technologies (1102). The arthroplasty jig blanks may all be of the same size, or may have different sizes. For example, in some variations, six different sizes of one type of arthroplasty jig blank may be formed. Each of the arthroplasty jig blanks has a left or right knee orientation. The arthroplasty jig blanks may be mass-produced, and typically are not initially patient-specific.

Next, appropriate sizes for a specific patient's femoral and/or tibial arthroplasty jigs are selected (1104) based on information gathered during preoperative planning (1106). The selected arthroplasty jig blanks may then undergo a marking/labeling process (1108) using, for example, laser technology, printing technology, machine engraving, and/or adhesive labeling. Examples of information that may be included on the arthroplasty jig blanks include patient names, doctor names, company logos, barcodes, etc. Marking and labeling are described, for example, in U.S. patent application Ser. No. 11/642,385, filed on Dec. 19, 2006, which is hereby incorporated by reference in its entirety. Next, a machining process is performed to add patient-specific features to the femoral and tibial arthroplasty jig blanks, in addition to other features, such as guiding slots and/or holes (1110). The resulting patient-specific arthroplasty jigs may then undergo a cleaning process (1112) and a packaging process (1114). Thereafter, the packaged arthroplasty jigs may be sterilized (1116) using, for example, gamma radiation, e-beam radiation, and/or one or more other methods. The sterilized arthroplasty jigs may then be shipped to designated hospitals (1118).

Figure 12A:
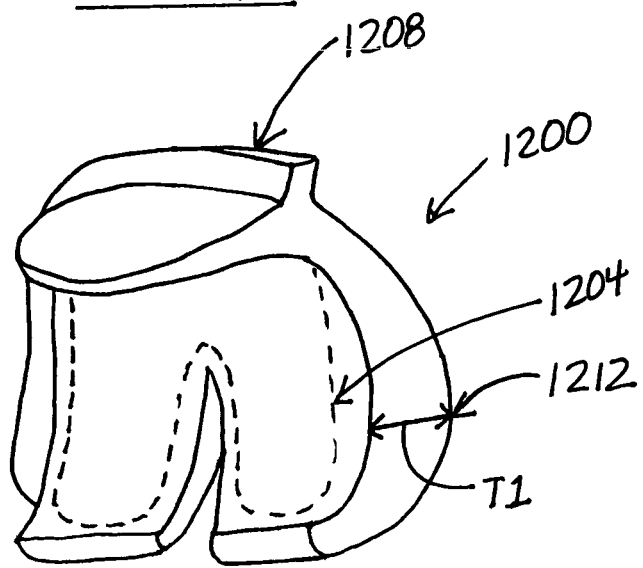
FIG. 12A is a perspective view of a near-shape femoral arthroplasty jig blank.
Figure 12B:
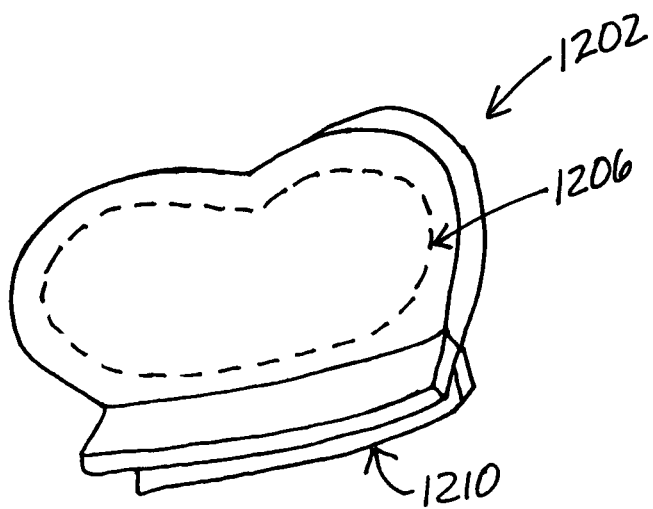
FIG. 12B is a perspective view of a near-shape tibial arthroplasty jig blank.

FIG. 12A shows a near-shape femoral arthroplasty jig blank (1200), and FIG. 12B shows a near-shape tibial arthroplasty jig blank (1202). Although these near-shape arthroplasty jig blanks do not include patient-specific features, they have shapes that are similar to the shapes of the arthroplasty jigs that will eventually be formed from them. Use of near-shape arthroplasty jig blanks to form customized arthroplasty jigs may accelerate the arthroplasty jig manufacturing process (e.g., relative to a process in which arthroplasty jigs are formed from feature-less arthroplasty jig blanks). Dotted lines (1204) and (1206) represent the locations on the near-shape arthroplasty jig blanks at which patient-specific features will be added during an arthroplasty jig formation process, such as the arthroplasty jig formation process described above with reference to FIG. 11. It should be noted that these are only exemplary locations at which patient-specific features will be added, and other locations may alternatively or additionally be used. Features (1208) and (1210) are included on near-shape femoral arthroplasty jig blank (1200) and near-shape tibial arthroplasty jig blank (1202), respectively, and are configured to function as reciprocal saw guides. Relatively thick areas of the near-shape arthroplasty jigs (relative to other areas of the jigs) may represent the location of drill holes that may provide a long and stable bushing. An example of a relatively thick area is area (1212) of near-shape femoral arthroplasty jig blank (1202), which has a thickness (T1). In some variations, the corresponding thickness of the femoral arthroplasty jig that results from femoral arthroplasty jig blank (1202) may be equal to or less than about 30% of thickness (T1).

Figure 13A:
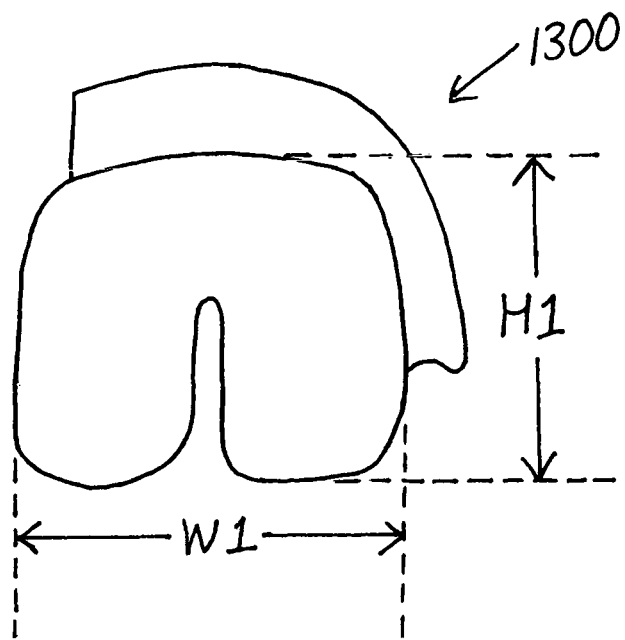
FIG. 13A is a front view of a near-shape femoral arthroplasty jig blank.
Figure 13B:
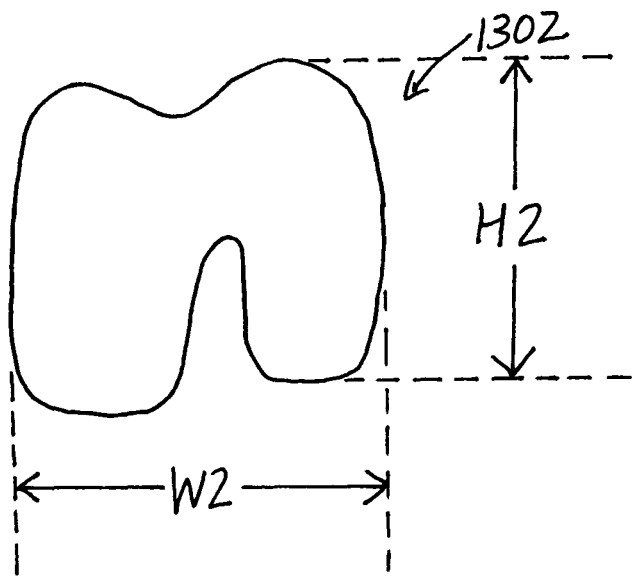
FIG. 13B is a front view of a femoral arthroplasty implant.

In some variations, one or more of the features of a near-shape arthroplasty jig blank may be designed or selected based on the corresponding implant that will be used. As an example, FIGS. 13A and 13B are front views of a near-shape femoral arthroplasty jig blank (1300) and its corresponding femoral arthroplasty implant (1302). There are, for example, six different sizes of Vanguard™ prosthetic femoral arthroplasty implants (manufactured by Biomet, Inc.). It is believed that these six different sizes may cover more than 90% of total knee arthroplasty surgeries. The dimensions of the near-shape arthroplasty jig blanks can be designed and selected with reference to the dimensions of one of these implants, or with reference to another appropriate implant, such as the Triathlon® Knee System (from Stryker® Orthopaedics), the P.F.C.® Sigma Knee System (from DePuy), etc.

As shown in FIGS. 13A and 13B, near-shape femoral arthroplasty jig blank (1300) has a width (W1) that is greater than the corresponding implant width (W2). The difference between width (W1) and width (W2) may be, for example, at least three millimeters. Similarly, near-shape femoral arthroplasty jig blank (1300) has a height (H1) that is greater than the corresponding implant height (H2). The difference between height (H1) and height (H2) may be, for example, at least three millimeters. Additionally, in some variations, an arthroplasty jig may have a thickness of from four millimeters to ten millimeters. If the near-shape femoral arthroplasty jig blanks are modeled based on the Vanguard™ femoral arthroplasty implants, for example, then there may be at least six near-shape femoral arthroplasty jig blanks available, which may cover 90% of TKA patients' knees. However, any resulting arthroplasty jigs may be modified. For example, in some variations, the outer boundary of an arthroplasty jig may be further machined down (e.g., to provide a smaller arthroplasty jig size for a minimally invasive TKA surgery). Furthermore, an arthroplasty jig for a knee that is much bigger or much smaller than the sizes of the available near-shape arthroplasty jig blanks may be made using one or more other manufacturing technologies, such as selective laser sintering (SLS), SLA methods, etc.

Figure 14A:
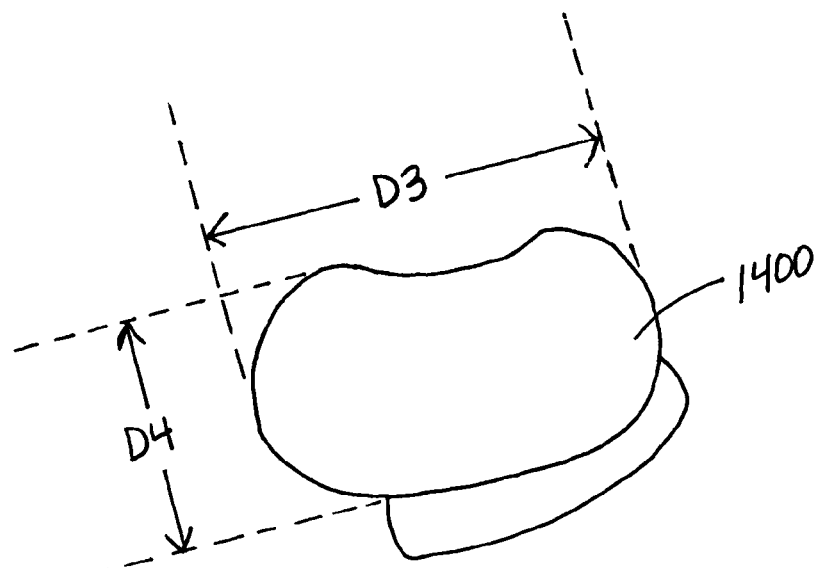
FIG. 14A is a front view of a near-shape tibial arthroplasty jig blank.
Figure 14B:
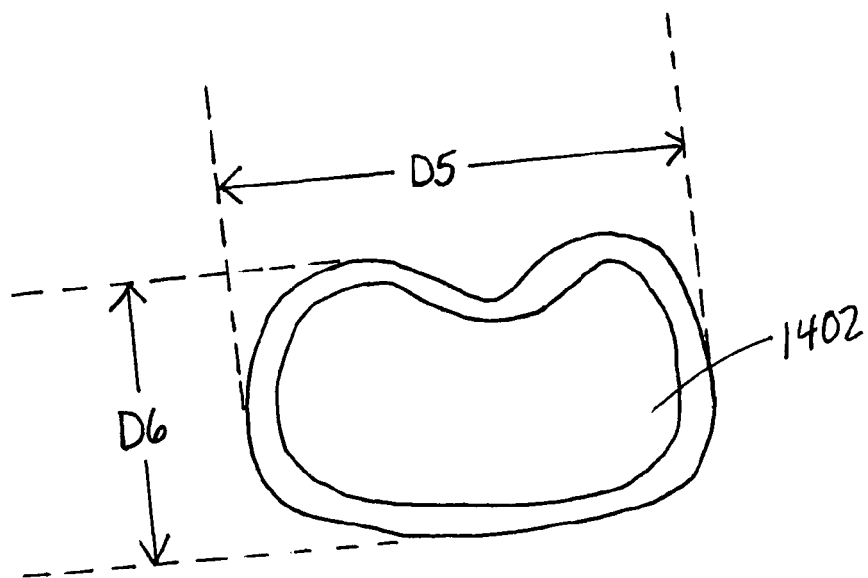
FIG. 14B is a front view of a tibial arthroplasty implant.

FIGS. 14A and 14B show top views of a near-shape tibial arthroplasty jig blank (1400) and its corresponding prosthetic tibial arthroplasty implant (1402). As with the Vanguard™ prosthetic femoral arthroplasty implants described above, there are six different sizes of Vanguard™ prosthetic tibial arthroplasty implants (manufactured by Biomet, Inc.). However, dimensions (D3) and (D4) of near-shape tibial arthroplasty jig blank (1400) are smaller than the corresponding dimensions (D5) and (D6) of tibial arthroplasty implant (1402). This helps to limit the likelihood of potential interference by soft tissue. Accordingly, near-shape tibial arthroplasty jig blank (1400) may be made to cover 50-90% of tibial articular surface and exposed proximal tibial cortical bone. Additionally, the outer boundary of the resulting tibial arthroplasty jig may be further machined down to provide an optimal fitting of the tibial arthroplasty jig with the tibial plateau during surgery.

Figure 15:
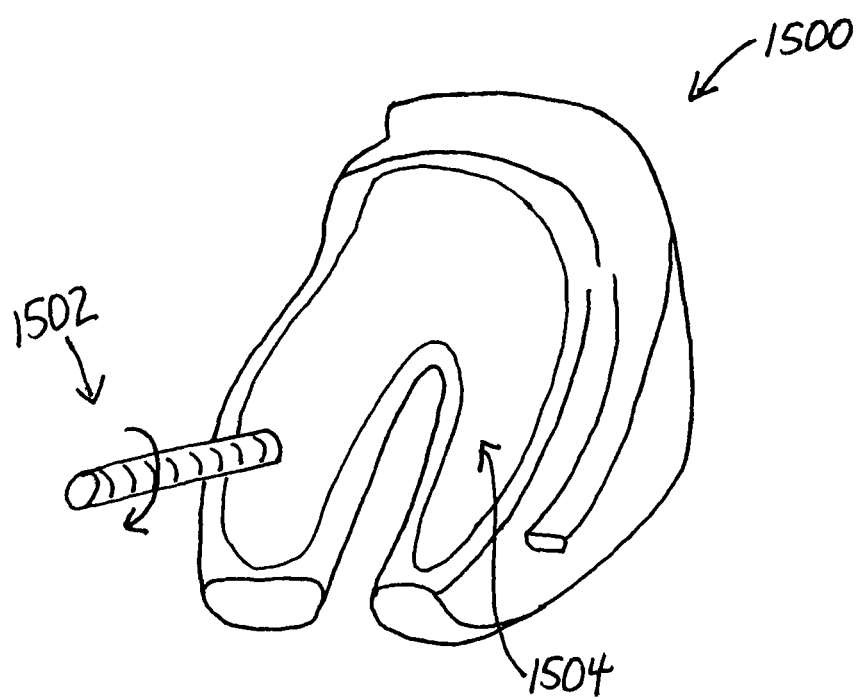
FIG. 15 is a perspective view of a near-shape femoral arthroplasty jig blank undergoing a milling process.

FIG. 15 shows a near-shape femoral arthroplasty jig blank (1500) undergoing a milling process (1502) to add patient-specific features (1504) onto the arthroplasty jig blank. The patient-specific features may be added based on preoperative planning information, which may include the anatomical shape of the patient's articular cartilage surface and exposed and side distal femur cortical bone (obtained, for example, from MRI and/or CT images). A machining file may be generated based on this preoperative planning information, and may be used to provide a CNC machine and/or an automated mechanical system (e.g., a robot) with instructions to machine patient-specific cavities and/or other features onto the arthroplasty jig blank.

Figure 16:
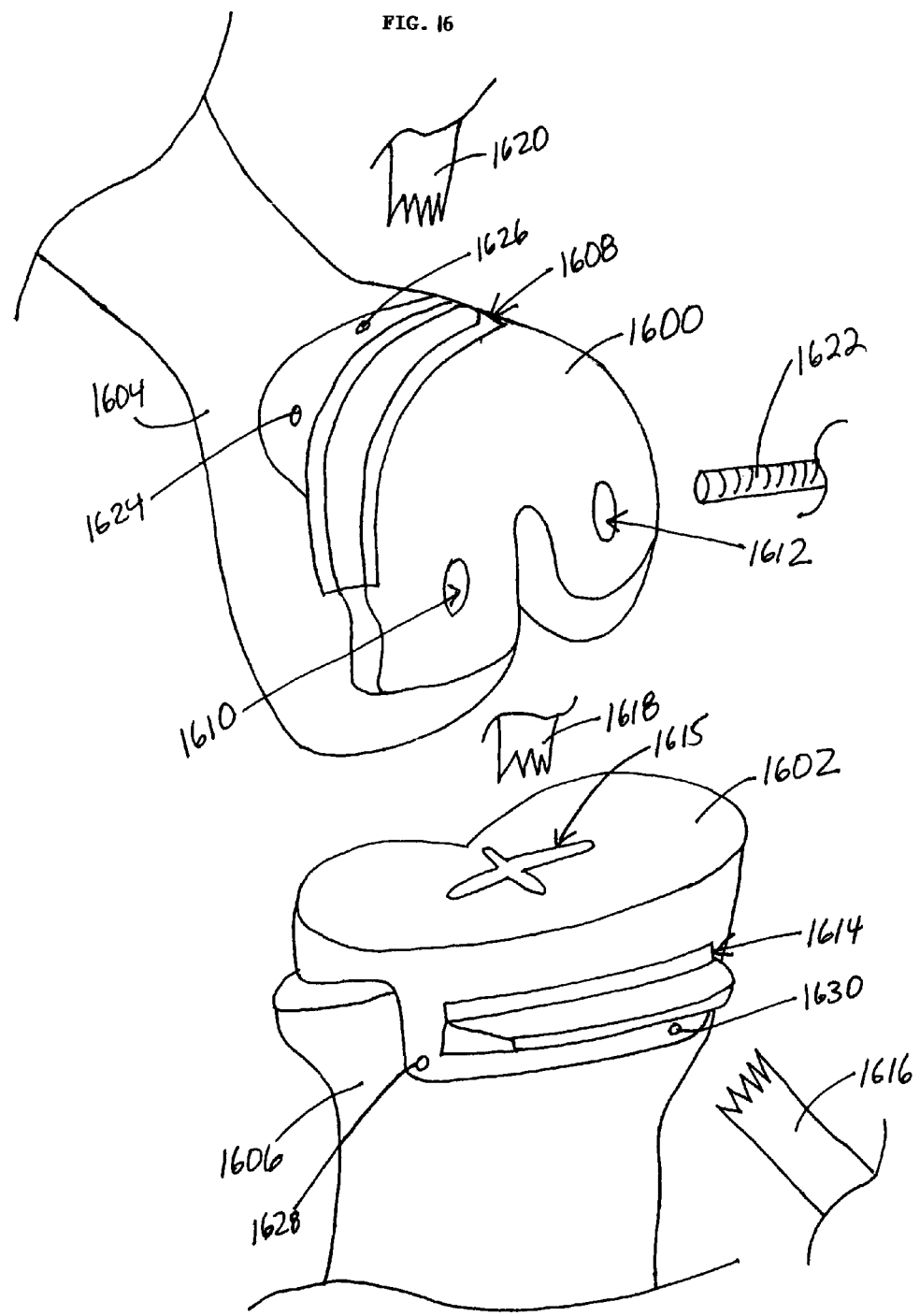
FIG. 16 illustrates the use of customized femoral and tibial arthroplasty jigs on a femur and a tibia of a subject, respectively.

FIG. 16 is a perspective view of customized (patient-specific) femoral and tibial arthroplasty jigs (1600) and (1602), respectively. Femoral arthroplasty jig (1600) is attached to a distal region of a femur (1604), while tibial arthroplasty jig (1602) is attached to a proximal region of a tibia (1606). Femoral arthroplasty jig (1600) includes a slot (1608) and holes (1610) and (1612), while tibial arthroplasty jig (1602) includes slots (1614) and (1615). These features may be machined, for example, based on preoperative planning information regarding patient-specific anatomical cavity features. Once an incision has been made and the distal region of the femur and proximal region of the tibia have been exposed in the operating room, the customized arthroplasty jigs may be precisely matched with anatomical surfaces of the knee. Moreover, the slots and holes in the customized arthroplasty jigs may be used to guide one or more osteotomy instruments. The osteotomy instruments may be cutting instruments, such as reciprocal saws (1616), (1618), and/or (1620), and/or drilling instruments, such as stem drill (1622). The above-described slots and holes, in addition to jig fixation holes (1624), (1626), (1628), and (1630) on the femoral and tibial arthroplasty jigs, may provide for relatively high-precision cutting and drilling based on preoperative planning.

The arthroplasty jigs and arthroplasty jig blanks described herein may be formed of any of a number of different materials. They may be formed of just one material, or multiple materials, such as a blend of different materials or layers of different materials. Generally, the arthroplasty jigs and arthroplasty jig blanks may be formed of any suitable biocompatible material. Examples of suitable materials include polymers, metals, ceramics, metal alloys, and combinations thereof. Specific examples of polymers include acetal resins (e.g., Delrin®), polyetheretherketones (PEEK), polycarbonates, polyamides, polyesters, polystyrenes, polyacrylates, vinyl polymers, and polyurethanes. Specific examples of metals and metal alloys include gold, platinum, palladium, stainless steel, cobalt alloys (e.g., Elgiloy®), and nickel-titanium alloys (e.g., Nitinol™). In some variations, the arthroplasty jig blanks may be formed of one or more plastics. In such variations, the blanks may be formed, for example, using injection molding technology and/or thermal plastic press forming technology. In certain variations, an arthroplasty jig may be intended to be disposable, and in some variations, an arthroplasty jig may be intended to be recyclable. The materials out of which an arthroplasty jig is formed may be selected with these and/or other criteria in mind. As an example, some variations of arthroplasty jigs may be formed of thermoplastic materials, and may be 100% recyclable. Moreover, certain variations of arthroplasty jigs may be formed of two or more layers of different materials, and/or may include one or more coatings.

Figure 17:
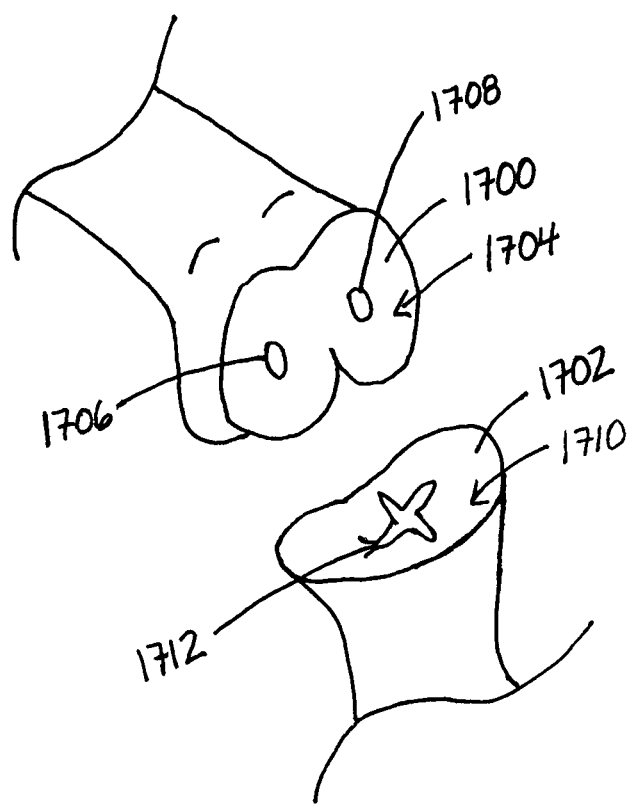
FIG. 17 is a perspective view of a distal portion of a femur of a subject and a proximal portion of a tibia of the subject, after resection using customized arthroplasty jigs.

FIG. 17 shows a distal region of a femur (1700) and a proximal region of a tibia (1702) after they have been resected using customized arthroplasty jigs, such as those described above. Femur (1700) includes a femoral distal cut (1704) and two stem drilling holes (1706) and (1708). Tibia (1702) includes a tibial cut (1710) and a tibial stem cut (1712). These cuts can be important to the successful alignment of prosthetic implants in these regions, such that excellent extension and flexion of the knee joint are provided.

Figure 18:
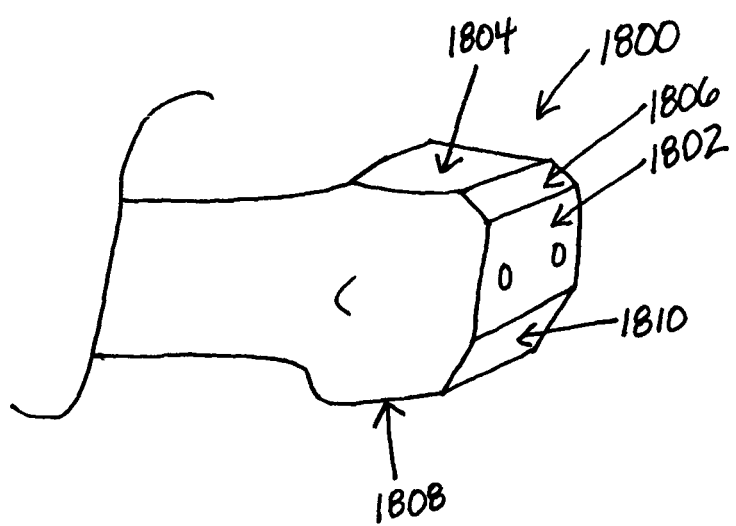
FIG. 18 is a perspective view of a distal portion of a femur of a subject after resection and drilling.

FIG. 18 shows additional different types of cuts that may be made to a femur (1800) during a knee arthroplasty procedure. As shown in FIG. 18, a distal portion of femur (1800) has been resected to provide a femoral distal cut (1802) for the translation position of a femoral implant. The femoral distal cut may be formed using, for example, a distal resector (available as part of the Vanguard™ Knee System, from Biomet, Inc.). Additional cuts that have been made to femur (1800) include a posterior resection (1804), a posterior anterior chamfer resection (1806), an anterior resection (1808), and a posterior chamfer resection (1810). These four resections may be formed using, for example, a sliding 4-in-1 cut block (also available as part of the Vanguard™ Knee System, from Biomet, Inc.).

Figure 19A:
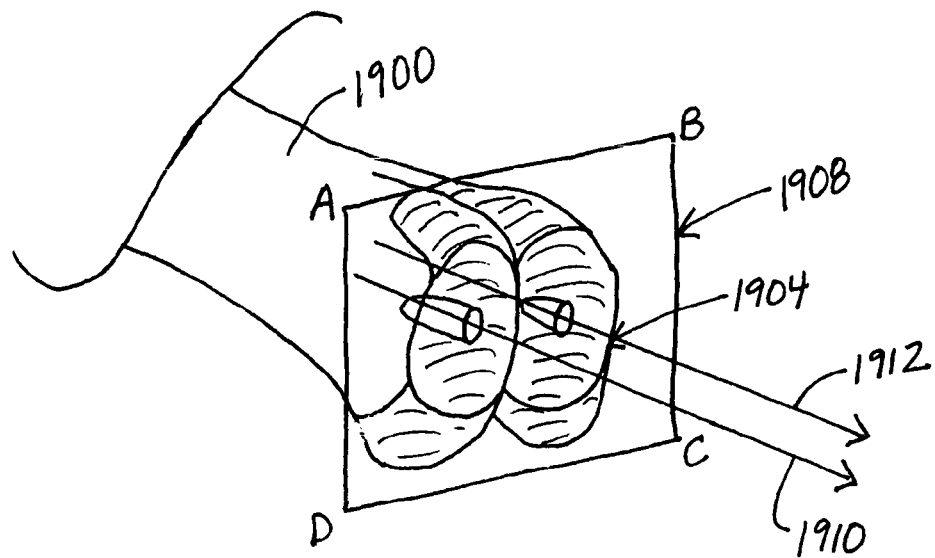
FIG. 19A is an illustration of preoperative planning data of a distal portion of a femur of a subject.
Figure 19B:
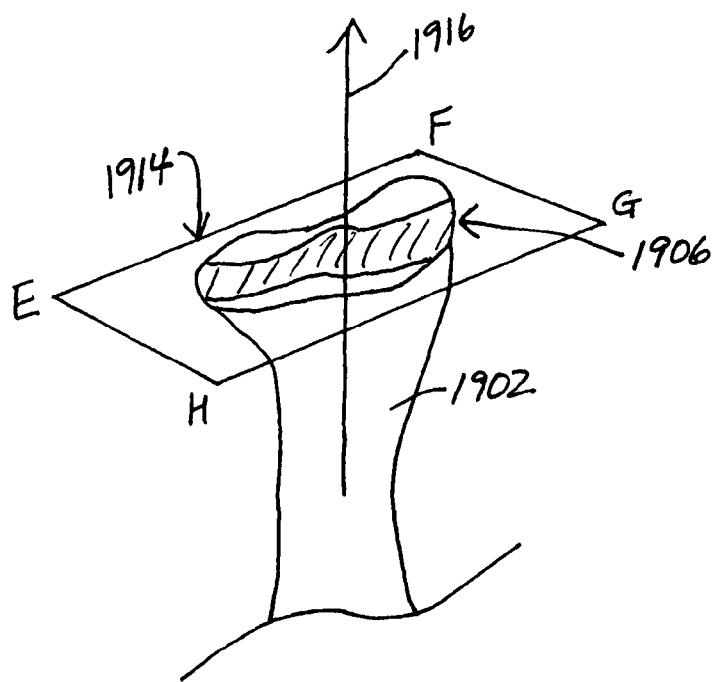
FIG. 19B is an illustration of preoperative planning data of a proximal portion of a tibia of a subject.

FIGS. 19A and 19B show three-dimensional computer models based on preoperative planning information of a patient's femur and tibia. The three-dimensional computer models include a model of the femur (1900) and a model of the tibia (1902), and may be formed from multiple segmented images of the patient's femur and tibia, obtained using MRI, CT, and/or one or more other imaging technologies. The preoperative planning that is performed may be based on a traditional TKA surgical method, a shape-matching method, and/or one or more other preferred methods. Once the appropriately sized femoral and tibial implants have been selected based on the results of the preoperative planning, the selected three-dimensional implant computer models (as shown, femoral implant model (1904) and tibial implant model (1906)) are automatically superposed onto the three-dimensional femoral and tibial computer models (1900) and (1902). This may be accomplished using computer-aided graphics including positioning algorithms (e.g., using one or more of the software programs described above). Based on the superpositions between the three-dimensional femoral and tibial computer models and their corresponding three-dimensional implant computer models, certain cut planes and stem directions may be obtained. For example, and as shown in FIG. 19A, a distal cut plane (1908) (formed from points A, B, C, and D) and two femoral stem directions (1910) and (1912) are obtained. Similarly, and as shown in FIG. 19B, a tibial cut plane (1914) (formed from points E, F, G, and H) and a tibial stem direction (1916) are obtained. These cut planes and stem directions may provide important information with regard to the alignment of prosthetic implants in the preoperative planning process.

Figure 20A:
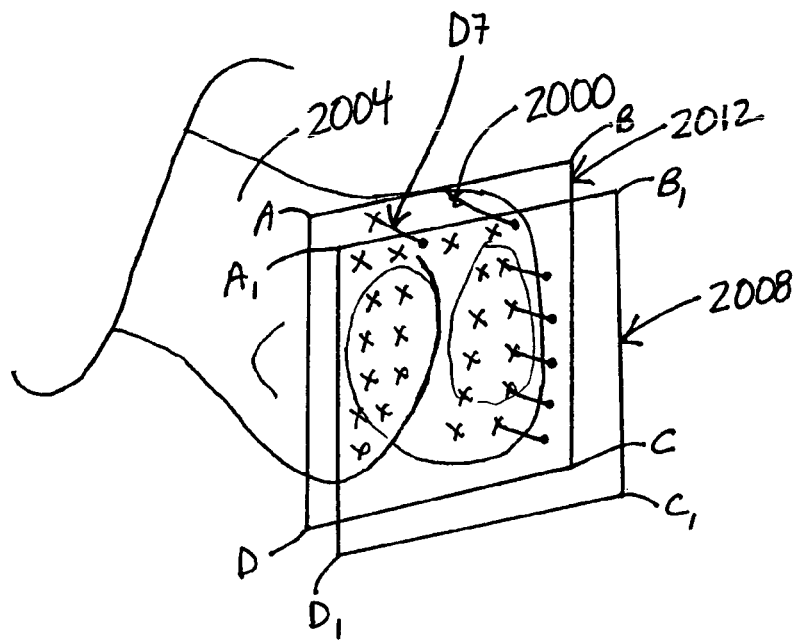
FIG. 20A is a perspective view of a computer-aided point-to-point matching process for a distal portion of a femur of a subject.
Figure 20B:
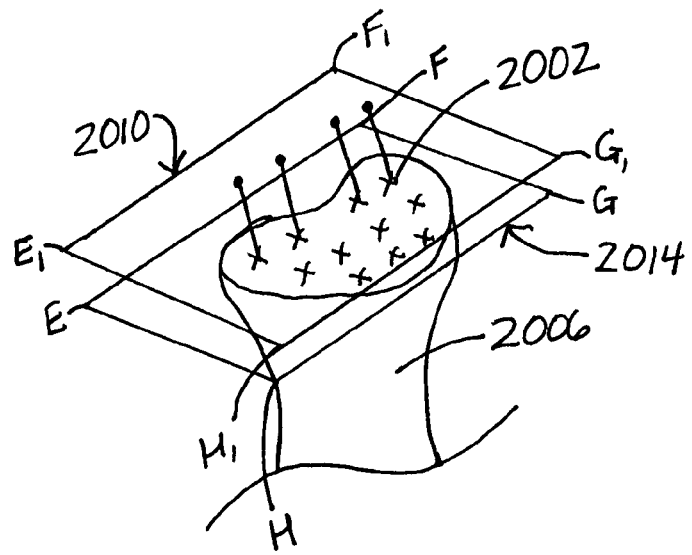
FIG. 20B is a perspective view of a computer-aided point-to-point matching process for a proximal portion of a tibia of a subject.

FIGS. 20A and 20B illustrate a computer-aided point-to-point mapping process that can be used to map a distal portion of a subject's femur, and a proximal portion of the subject's tibia. First, a total number of N points, such as point (2000) and point (2002), are selected on the surfaces of the articular cartilage and bone of a femur (2004) and a tibia (2006). In mapping femur (2004), the distance (such as distance (D7)) between each point on a femoral distal cut plane (2012) formed from points A, B, C, and D, to a corresponding point on a parallel reference femoral plane (2008) formed from points $A_1, B_1, C_1$, and $D_1$, is measured and registered for all N points. Generally, as N increases, accuracy of implant alignment can become enhanced. Tibial mapping is similar, except that the distances are measured from each point on a tibial cut plane (2014) formed from points E, F, G, and H, to a corresponding point on a parallel reference tibial plane (2010) formed from points $E_1, F_1, G_1$, and $H_1$.

Figure 21A:
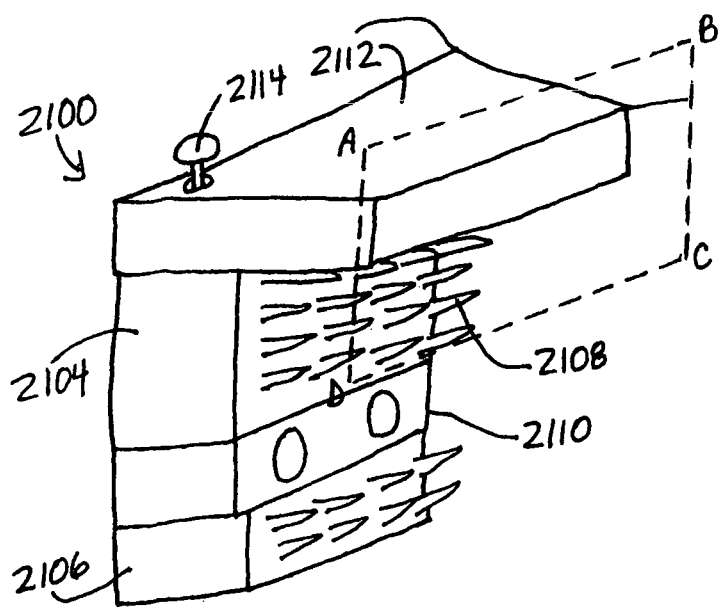
FIG. 21A is a perspective view of a femoral multi-pin guided device.
Figure 21B:
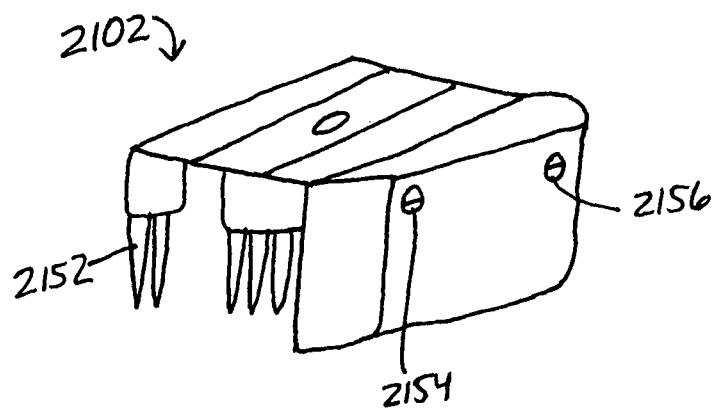
FIG. 21B is a perspective view of a tibial multi-pin guided device.

Certain devices may be used to help properly position an arthroplasty jig at a target site. For example, FIG. 21A shows a multi-pin guided device (2100) that may be used for aligning an arthroplasty jig on a distal portion of a subject's femur, while FIG. 21B shows a multi-pin guided device (2102) that may be used for aligning an arthroplasty jig on a proximal portion of a subject's tibia.

Femoral device (2100) includes pin blocks (2104) and (2106) holding N number of pins, such as pin (2108). In some variations, N may be greater than three and less than 1,000. Each pin is a mechanical registration pin in the form of a rod with a rounded edge that is configured to contact cartilage or bone during surgery. Each pin is arranged to match a corresponding distance registered in a point-to-point matching process performed previously (such as distance (D7), described with reference to FIG. 20A). Furthermore, device (2100) includes a drill bushing block (2110) that is positioned between pin blocks (2104) and (2106), and that can provide a surgeon with femoral prosthetic implant stem hole positions. An instrument guiding block (2112) is placed on top of pin blocks (2104) and (2106), to guide an arthroplasty jig to form a femoral distal cut corresponding to plane ABCD (such as femoral distal cut (1802) shown in FIG. 18). Device (2100) further includes a feature (2114) that functions as a mechanical tightening device by firmly securing the multiple blocks and pins for final assembly.

Similarly, tibial device (2102) is a multiple pin-based mechanical jig guiding device. While tibial device (2102) has a different configuration from femoral device (2100), tibial device (2102) has similar components to femoral device (2100). For example, tibial device (2102) includes pins (e.g., pin 2152) and features (2154) and (2156) that function as mechanical tightening devices by firmly securing the multiple blocks and pins of tibial device (2102) for final assembly.

Figure 21C:
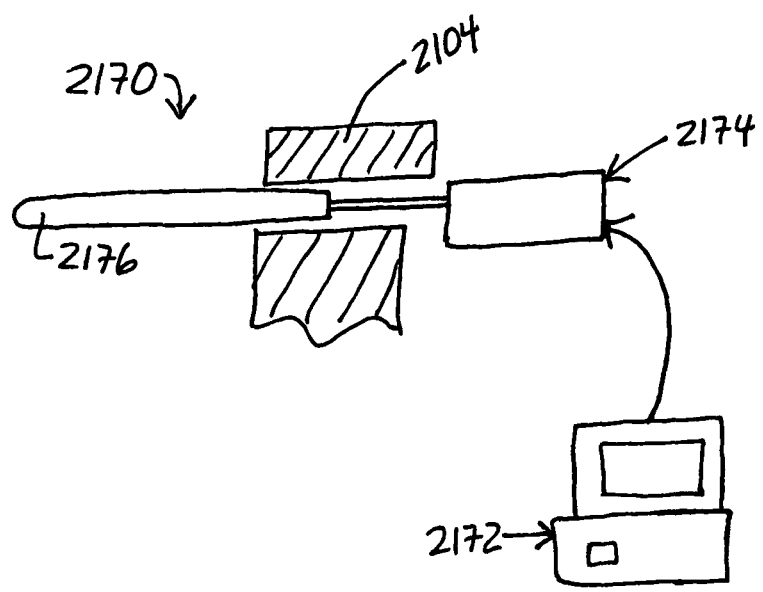
FIG. 21C is a schematic diagram of a computer-aided manufacturing process for forming multi-pin guided devices.

Tibial device (2102) and femoral device (2100) may be assembled manually (e.g., by surgeons, nurses, or any other qualified personnel), or may be assembled using a device such as computer-controlled positioning device (2170), shown in FIG. 21C. Device (2170) includes a computer program (2172) (e.g., for use with a PC) that controls multiple actuators (2174) or a similar device that push pins, such as pin (2176), into one of the pin blocks (as shown, pin block (2104)). Actuators (2174) also can position all of the blocks of the device based on preoperative planning data. The assembly of multi-pin guided devices may be done either preoperatively (i.e., before a surgical incision) or intraoperatively (i.e., after a surgical incision has been made).

FIG. 22 illustrates the positioning of conventional arthroplasty jig instruments, using multi-pin guided surface-matching devices, on a distal portion of a patient's femur and a proximal portion of the patient's tibia. After the distal femoral portion (2200) and the proximal tibial portion (2202) have been exposed via an incision, the multi-pin guided devices (2204) and (2206) are used to match the surfaces of the femur and the tibia, respectively. The positions are uniquely defined according to the plan (i.e., one-to-one matching). First, stem hole drilling processes (2208) and (2210) are performed with respect to the drill hole bushings (2212), (2214), and (2216) assembled in the multiple pin based mechanical jig guiding devices. A distal resector (2218), which is a conventional TKA jig instrument, is placed with respect to multi-pin guided device (2204) and is firmly fixed onto the anterior side of the femur with multiple nails and/or screws (2220) and (2222). The multi-pin guided surface matching device (2204) may then be removed, and a surgeon may make a femoral distal cut using a reciprocal saw (2224). Tibial resection may be done similarly to the femoral distal resection, as shown.

While the multi-pin guided surface matching devices described above have been described with reference to their use in positioning arthroplasty jigs, in some variations, an arthroplasty jig itself may be in the form of a multi-pin device. The pins may be used, for example, the help accurately position the arthroplasty jig at a target site. Arthroplasty jigs including positioning components are described, for example, in U.S. patent application Ser. No. 11/642,385, filed on Dec. 19, 2006, which was previously incorporated by reference in its entirety. An arthroplasty jig that is in the form of a multi-pin device may be formed using preoperative and/or intraoperative planning methods, and may be used, for example, in point-to-point matching.

The methods and devices described herein have been described with respect to arthroplasty jigs. However, the features of the methods and devices described herein may apply to some variations of implants, such as arthroplasty implants. Moreover, while arthroplasty procedures have been described, the jigs and implants described herein may be used in any of a number of different procedures, including, for example, spinal surgery.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A method of manufacturing a patient specific arthroplasty jig, the method comprising:
   providing a near-shape jig blank to a manufacturing machine, the near-shape jig blank having a first outer surface having a pair of generally orthogonal surfaces, a second outer surface opposite the first outer surface, and a feature that will be retained in the patient specific arthroplasty jig, the feature including a general shape of the near-shape jig blank, the general shape being specific to either a right knee or a left knee;
   using the manufacturing machine to create the patient specific arthroplasty jig from the near-shape jig blank by generating in the first outer surface of the near-shape jig blank patient specific features including a matching surface corresponding to an articular surface of a knee of a patient, the matching surface being generated preoperatively using a computer and determined from a preoperative analysis of image data of the articular surface of the knee of the patient, the matching surface being configured to mechanically register to the articular surface; and
   using the manufacturing machine to generate in the near-shaped jig blank a saw guiding slot, the saw guiding slot being generated preoperatively.

2. The method of claim 1, wherein the matching surface is generated in the near-shape jig blank by the manufacturing machine via machining.

3. The method of claim 1, wherein the saw guiding slot is generated in the near-shape jig blank by the manufacturing machine via machining.

4. The method of claim 1, wherein the patient specific arthroplasty jig is for total knee arthroplasty.

5. A method of manufacturing a patient specific arthroplasty jig, the method comprising:
   providing a near-shape jig blank to a manufacturing machine, the near-shape jig blank having a first outer surface having a pair of generally orthogonal surfaces, a second outer surface opposite the first outer surface, and a feature that will be retained in the patient specific arthroplasty jig, the feature including a general shape of the near-shape jig blank, the general shape being specific to either a femur or tibia;
   using the manufacturing machine to create the patient specific arthroplasty jig from the near-shape jig blank by generating in the first outer surface of the near-shape jig blank patient specific features including a matching surface corresponding to an articular surface of a knee of a patient, the matching surface being generated preoperatively using a computer and determined from a preoperative analysis of image data of the articular surface of the knee of the patient, the matching surface being configured to mechanically register to the articular surface; and
   using the manufacturing machine to generate in the near-shaped jig blank a saw guiding slot, the saw guiding slot being generated preoperatively.

6. The method of claim 5, wherein the matching surface is generated in the near-shape jig blank by the manufacturing machine via machining.

7. The method of claim 6, wherein the saw guiding slot is generated in the near-shape jig blank by the manufacturing machine via machining.

8. The method of claim 7, wherein the patient specific arthroplasty jig is for total knee arthroplasty.

9. A method of manufacturing a patient specific arthroplasty jig, the method comprising:
   selecting a size category from an inventory of multiple size categories of near-shape jig blanks based on a dimension associated with a knee of a patient, each jig blank having a first outer surface having a pair of generally orthogonal surfaces, second outer surface opposite the first outer surface, and a feature that will be retained in the patient specific arthroplasty jig;
   obtaining a near-shape jig blank from the selected size category;
   using a manufacturing machine to create the patient specific arthroplasty jig from the near-shape jig blank by generating in the near-shape jig blank patient specific features including a matching surface corresponding to an articular surface of the knee of the patient, the matching surface being generated preoperatively using a computer and determined from a preoperative analysis of image data of the articular surface of the knee of the patient, the matching surface being configured to mechanically register to the articular surface; and
   using the manufacturing machine to generate in the near-shaped jig blank a saw guiding slot, the saw guiding slot being generated preoperatively.

10. The method of claim 9, wherein the matching surface is generated in the near-shape jig blank by the manufacturing machine via machining.

11. The method of claim 9, wherein the saw guiding slot is generated in the near-shape jig blank by the manufacturing machine via machining.

12. The method of claim 9, wherein the patient specific arthroplasty jig is for total knee arthroplasty.

13. The method of claim 9, wherein there are at least six size categories.

14. The method of claim 9, wherein the dimension includes a medial/lateral dimension.

15. The method of claim 9, wherein the dimension includes an anterior/posterior dimension.

16. The method of claim 9, wherein each size category includes orientation categories including a right knee orientation category and a left knee orientation category, the method further comprising preoperatively making a right-left determination of whether the knee of the patient is right or left and using the right-left determination to select an orientation category.

17. The method of claim 16, wherein the obtaining the near-shape jig blank from the selected size category also includes obtaining the near-shape jig blank from the selected orientation category.

18. The method of claim 9, wherein each size category includes bone-type categories including a femur category and a tibia category, the method further comprising preoperatively making a femur-tibia determination of whether the patient specific arthroplasty jig should be a femur jig or a tibia jig and using the femur-tibia determination to select a bone-type category.

19. The method of claim 18, wherein the obtaining the near-shape jig blank from the selected size category also includes obtaining the near-shape jig blank from the selected bone-type category.

20. A method of manufacturing a patient specific arthroplasty jig, the method comprising:

preoperatively analyzing image data of an articular surface of bone of a patient;

using a computer, preoperatively computer modeling a matching surface corresponding to at least a portion of the articular surface;

providing a near-shape jig blank to a manufacturing machine, the near-shape jig blank having a first outer surface having a pair of generally orthogonal surfaces, a second outer surface opposite the first outer surface, and a feature that will be retained in the patient specific arthroplasty jig, wherein the feature is at least one of: a) that the near-shape jig blank is only for a right knee or a left knee; b) that the near-shape jig blank is only for a femur or tibia; or c) that the near-shape jig blank is only for a certain selected size of jig associated with at least one dimension of the bone; and using the manufacturing machine to preoperatively create the patient specific arthroplasty jig from the near-shape jig blank by generating in the first outer surface of the near-shape jig blank patient specific features including the matching surface, the matching surface being configured to mechanically register to the at least a portion of the articular surface.

21. The method of claim 20, further comprising using the manufacturing machine to generate in the near-shaped jig blank a saw guiding slot, the saw guiding slot being generated preoperatively.

22. A method of manufacturing a patient specific arthroplasty jig for use on a knee of a patient, the knee include a medial and a lateral condyle surface, the method comprising:

providing a near-shape jig blank to a manufacturing machine, the near-shape jig blank having a first outer surface having geometrically distinct condyle portions corresponding to the respectively medial and the lateral condyle surfaces; and using the manufacturing machine to create the patient specific arthroplasty jig from the near-shape jig blank by generating patient specific features in the first outer surface of the near-shape jig blank, the patient specific features including a matching surface corresponding to an articular surface of a knee of a patient, the matching surface being generated preoperatively using a computer and determined from a preoperative analysis of image data of the articular surface of the knee of the patient, the matching surface being configured to mechanically register to the articular surface.

23. The method of claim 22, further comprising generating in the near-shaped jig blank a saw guiding slot the saw guiding slot being generated preoperatively.

24. The method of claim 22, wherein a shape of the geometrically distinct condyle portions of the near-shape jig blank is different for a femur and a tibia.

25. The method of claim 22, wherein a shape of the geometrically distinct condyle portions of the near-shape jig blank is different for a right knee and a left knee.

26. The method of claim 22, further comprising a second outer surface opposite the first outer surface, the second outer surface including a shape configuration that approximates that of the patient specific arthroplasty jig.

27. The method of claim 22, wherein an indent separates the geometrically distinct condyle portions.

28. The method of claim 1, wherein the image data is generated from CT or MRI images of the knee of the patient.

29. The method of claim 5, wherein the image data is generated from CT or MRI images of the knee of the patient.

30. The method of claim 9, wherein the image data is generated from CT or MRI images of the knee of the patient.

31. The method of claim 20, wherein the image data is generated from CT or MRI images of the knee of the patient.

32. The method of claim 22, wherein the image data is generated from CT or MRI images of the knee of the patient.

33. The method of claim 1, wherein the manufacturing machine is a CNC machine.

34. The method of claim 5, wherein the manufacturing machine is a CNC machine.

35. The method of claim 9, wherein the manufacturing machine is a CNC machine.

36. The method of claim 20, wherein the manufacturing machine is a CNC machine.

37. The method of claim 22, wherein the manufacturing machine is a CNC machine.

* * * * *